(12) United States Patent
Wong et al.

(10) Patent No.: US 11,169,111 B2
(45) Date of Patent: Nov. 9, 2021

(54) APPARATUSES, METHODS, SYSTEMS, AND COMPUTER-READABLE MEDIA FOR FLUID POTENTIAL ARTIFACT CORRECTION IN REAGENT DELIVERY SYSTEMS

(71) Applicant: LIFE TECHNOLOGIES CORPORATION, Carlsbad, CA (US)

(72) Inventors: Chiu Tai Andrew Wong, Orange, CT (US); Todd Rearick, Cheshire, CT (US); John Donohue, Southbury, CT (US)

(73) Assignee: Life Technologies Corporation, Carlsbad, CA (US)

( * ) Notice: Subject to any disclaimer, the term of this patent is extended or adjusted under 35 U.S.C. 154(b) by 417 days.

(21) Appl. No.: 16/362,367

(22) Filed: Mar. 22, 2019

(65) Prior Publication Data
US 2020/0041444 A1    Feb. 6, 2020

Related U.S. Application Data

(62) Division of application No. 14/853,026, filed on Sep. 14, 2015, now Pat. No. 10,416,112.
(Continued)

(51) Int. Cl.
*G01N 27/414*    (2006.01)
*G16B 30/00*    (2019.01)

(52) U.S. Cl.
CPC ......... *G01N 27/4145* (2013.01); *G16B 30/00* (2019.02)

(58) Field of Classification Search
None
See application file for complete search history.

(56) References Cited

U.S. PATENT DOCUMENTS

| 5,202,637 A | 4/1993 | Jones |
| 5,853,910 A | 12/1998 | Tomioka et al. |

(Continued)

FOREIGN PATENT DOCUMENTS

WO    WO-2016044141    3/2016

OTHER PUBLICATIONS

PCT/US2015/049935, Search Report and Written Opinion, dated Jan. 14, 2016.
(Continued)

*Primary Examiner* — Robert T. Crow

(57) ABSTRACT

A method for correcting nucleotide incorporation signals for fluid potential effects or disturbances arising in nucleic acid sequencing-by-synthesis includes: disposing a plurality of template polynucleotide strands in a plurality of defined spaces disposed on a sensor array, the template polynucleotide strands having a sequencing primer and a polymerase bound therewith; exposing the template polynucleotide strands to a series of flows of nucleotide species flowed through a fluid manifold, the fluid manifold comprising passages for flowing nucleotide species and a branch passage for flowing a solution, the branch passage comprising a reference electrode and a sensing electrode; obtaining a plurality of nucleotide incorporation signals corresponding to the plurality of defined spaces, the nucleotide incorporation signals having a signal intensity related to a number of nucleotide incorporations; and correcting at least some of the plurality of nucleotide incorporation signals for fluid potential effects or disturbances.

10 Claims, 22 Drawing Sheets

Related U.S. Application Data

(60) Provisional application No. 62/146,882, filed on Apr. 13, 2015, provisional application No. 62/050,377, filed on Sep. 15, 2014.

(56) References Cited

U.S. PATENT DOCUMENTS

| | | |
|---|---|---|
| 7,948,015 B2 | 5/2011 | Rothberg et al. |
| 8,545,248 B2 | 10/2013 | Davey et al. |
| 8,666,678 B2 | 3/2014 | Davey et al. |
| 2004/0238379 A1 | 12/2004 | Lindsay et al. |
| 2009/0026082 A1 | 1/2009 | Rothberg et al. |
| 2010/0137143 A1 | 6/2010 | Rothberg et al. |
| 2010/0282617 A1 | 11/2010 | Rothberg et al. |
| 2010/0300895 A1 | 12/2010 | Nobile et al. |
| 2012/0172241 A1 | 7/2012 | Rearick et al. |
| 2012/0173158 A1 | 7/2012 | Hubbell |
| 2012/0173159 A1 | 7/2012 | Davey et al. |
| 2012/0264621 A1 | 10/2012 | Hubbell et al. |
| 2013/0060482 A1 | 3/2013 | Sikora et al. |
| 2013/0231870 A1 | 9/2013 | Sugnet et al. |
| 2014/0202883 A1 | 7/2014 | Nobile et al. |

OTHER PUBLICATIONS

PCT/US2015/049935, Invitation to Pay Additional Search Fees, dated Nov. 5, 2015.

Savitzky & Golay, "Smoothing and Differentiation of Data by Simplified Least Squares Procedures," Analytical Chemistry, vol. 36, No. 8, pp. 1627-1639.

APPARATUSES, METHODS, SYSTEMS, AND COMPUTER-READABLE MEDIA FOR FLUID POTENTIAL ARTIFACT CORRECTION IN REAGENT DELIVERY SYSTEMS

CROSS-REFERENCE TO RELATED APPLICATIONS

This application is a divisional of U.S. patent application Ser. No. 14/853,026, filed on Sep. 14, 2015. U.S. patent application Ser. No. 14/853,026 claims benefit of U.S. Provisional Application No. 62/050,377, filed Sep. 15, 2014, and claims benefit of U.S. Provisional Application No. 62/146,882, filed Apr. 13, 2015. All applications referenced in this section are incorporated herein by reference; each in its entirety.

COMPUTER PROGRAM LISTING APPENDIX

This application contains a Computer Program Listing Appendix, which has been submitted as a file in ASCII format via EFS-Web and is hereby incorporated by reference in its entirety. Said ASCII file was created on Mar. 6, 2019, is 64,933 bytes bytes in size, and has been entered as file named LT00942DIV_Computer_Program_Listing.txt.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE DISCLOSURE

This application generally relates to apparatuses, methods, systems, and computer readable media for signal correction in reagent delivery systems, and, more specifically, to apparatuses, methods, systems, and computer readable media for fluid potential artifact correction in nucleic acid sequencing.

BACKGROUND

Semiconductor chips have been used to measure fluid potential. In some applications, fluid flow is measured across a semiconductor chip including a sensor array having a plurality of rows and columns of transistors. However, there are a number of obstacles in providing accurate measurement based on current techniques.

Disturbances in electrolyte potential lead to measurement error, and may be generated by the charging and discharging of parasitic capacitances in the sensor array. Furthermore, these disturbances are not uniform across the sensor array, as the disturbances are more common within rows of the array and are more pronounced when switching between middle and top/bottom rows of the array. Row select switching also couples undesired signals into the fluid via a capacitance of column metallization. In addition to this stray column-to-fluid coupling capacitance, measurement error may further be attributed to electrostatic discharge that couples into the fluid, fluid resistance, leakage resistance, and the like. These effects are complicated by fluid flow across the semiconductor chip. In view of the above, it would be advantageous to have a device for correcting these fluid potential artifacts.

Various instruments or systems, which include one or more semiconductor chips, for sequencing nucleic acid sequences include reagent delivery systems that use various fluidic communications to perform sequencing-by-synthesis, including, for example, the Ion PGM™ and Ion Proton™ Sequencers using Ion Torrent™ sequencing technology (see, e.g., U.S. Pat. No. 7,948,015 and U.S. Pat. Appl. Publ. Nos. 2010/0137143, 2009/0026082, and 2010/0282617, which are all incorporated by reference herein in their entirety). In order to increase accuracy of nucleic acid sequencing using these and other systems (such as, e.g., sequencing-by-hybridization, sequencing-by-ligation, etc.) that deliver reagents via fluid, there is a need for new methods, systems, and computer readable media for correcting sequencing signals in the presence of noise and/or artifacts that may arise due to various effects or disturbances related to fluid carrying and/or delivering reagents.

SUMMARY OF THE DISCLOSURE

Embodiments disclose apparatuses, methods, systems, and computer-readable media for fluid potential artifact correction in reagent delivery systems. Further, embodiments disclose methods and devices for measuring a reaction product. The following methods, systems, computer-readable media, and devices are exemplified in a number of implementations, some of which are summarized below and throughout the specification.

In one aspect, an apparatus for measuring a reaction product includes a device including a flow cell in fluid communication with an electronic sensor. A plurality of reagent reservoirs are provided to include a plurality of reagents. A fluid manifold is in fluidic communication with the plurality of reagent reservoirs. An outlet passage of the fluid manifold is in fluid communication with the flow cell. A reference electrode provides a reference voltage to the electronic sensor through fluid in the outlet passage and the flow cell. A sensor electrode is in electrical communication with the fluid of the outlet passage and the flow cell.

In a related aspect, the fluid manifold further includes a branch passage between the fluid manifold and the flow cell in fluid communication with the outlet passage. The reference electrode is disposed in contact with fluid within the branch passage. The reference electrode is free of direct contact with any reagent of the plurality of reagents when the any reagent flows through the outlet passage. The sensor electrode is disposed in contact with the fluid within the branch passage. The sensor electrode is disposed closer to the outlet passage than the reference electrode. The sensor electrode is free of direct contact with any reagent of the plurality of reagents when the any reagent flows through the outlet passage. A solution reservoir is provided in fluid communication with the branch passage.

In a related aspect, the device further includes a second electronic sensor not in fluid communication with the flow cell, the second electronic sensor including a gate electrode, and an output from the sensor electrode in electrical communication with the gate electrode. An amplifier is coupled to the sensor electrode and provides a reference voltage offset to the sensor electrode. The electronic sensor includes a field effect transistor having a gate electrode. The electronic sensor includes an ion sensitive field effect transistor.

In another aspect, an apparatus includes a flow cell including a fluid inlet and a fluid outlet. An array of electronic sensors are cooperatively engaged with the flow cell. Each of the electronic sensors includes a field effect transistor having a gate electrode. A first subset of the array of electronic sensors is exposed to a fluid within the flow cell. A second subset of the array of electronic sensors is free of contact with the fluid within the flow cell. A sensor electrode is in electrical communication with the first subset of the array of electronic sensors through fluid via the fluid inlet or the fluid outlet. An output of the sensor electrode is in electrical communication with the gate electrodes of the field effect transistors of the second subset of the array of electronic sensors.

In a related aspect, the array of electronic sensors is arranged in rows and columns. The second subset of the array of electronic sensors includes a column of electronic sensors. The output of the sensor electrode is in electrical communication with the each electronic sensor within the column of electronic sensors of the second subset of the array of electronic sensors. A fluid manifold is in fluid communication with a plurality of reagent reservoirs. The fluid manifold includes an outlet passage in fluid communication with the fluid inlet. The sensor electrode is in electrical communication with the second subset of the array of electronic sensors through a solution via the outlet passage.

In a related aspect, a branch passage is provided between the fluid manifold and the flow cell in fluid communication with the outlet passage. The sensor electrode is disposed in the branch passage. The reference electrode is disposed in contact with fluid within the branch passage. The reference electrode is free of direct contact with any reagent of the plurality of reagents when the any reagent flows through the outlet passage. The sensor electrode is disposed in contact with fluid within the branch passage. The sensor electrode is disposed closer to the outlet passage than the reference electrode. The sensor electrode is free of direct contact with any reagent of the plurality of reagents when the any reagent flows through the outlet passage.

In a related aspect, a solution reservoir is in fluid communication with the branch passage. The plurality of reagent reservoirs include a plurality of reagents. A reference electrode provides a reference voltage to the first subset of the array of electronic sensors through a solution via the fluid inlet or the fluid outlet. An array of wells provides fluid access to the gate electrodes of the field effect transistors of the first subset of the array of electronic sensors. An amplifier is disposed in electrical communication between the output of the sensor electrode and the gate electrodes of the field effect transistors of the second subset of the array of electronic sensors. The field effect transistors of the first subset of the array of electronic sensors include ion sensitive field effect transistors.

In another aspect, a method of measuring a reaction product includes flowing a reagent solution into a flow cell. The reagent solution reacts to provide a reaction product. The flow cell is in fluid communication with a first electronic sensor. A response of the first electronic sensor to the reaction product is measured, and a response of a second electronic sensor is measured. The second electronic sensor is in electrical communication with a sensor electrode in fluid communication with the flow cell. The second electronic sensor is not in fluid communication with the flow cell. The response of the first electronic sensor is adjusted based on the response of the second electronic sensor.

In a related aspect, a reference voltage is applied through a solution in fluid communication with the flow cell in fluid communication with the first electronic sensor. The reference voltage is applied by a reference electrode. The first electronic sensor and the second electronic sensor include field effect transistors. The field effect transistor of the first electronic sensor includes an ion sensitive field effect transistor.

In a related aspect, a solution flows through the sensor electrode. A response of the sensor electrode is measured through the solution. The response of the sensor electrode is amplified. An offset to the measured response of the sensor electrode is provided to center the measured response relative to a reference voltage. The response of the first electronic sensor is adjusted by scaling and subtracting the response of the second electronic sensor.

In another aspect, a method of measuring a reaction product includes flowing a reagent solution into a flow cell. The reagent solution reacts to provide a reaction product. The flow cell is in fluid communication with an array of electronic sensors cooperatively engaged with the flow cell. A first subset of the array of electronic sensors is exposed to the reagent solution within the flow cell. A second subset of the array of electronic sensors is free of contact with the reagent solution fluid within the flow cell. A response of the first subset of the array of electronic sensors to the reaction product is measured. A response of the second subset of the array of electronic sensors is measured. The second subset of the array of electronic sensors is in electrical communication with a sensor electrode in fluid communication with the flow cell. The response of the first subset of the array of electronic sensors is adjusted based on the response of the second subset of the array of electronic sensors.

In a related aspect, each of the electronic sensors includes a field effect transistor having a gate electrode. The sensor electrode is in electrical communication with the first subset of the array of electronic sensors through fluid. An output of the sensor electrode is in electrical communication with the gate electrodes of the field effect transistors of the second subset of the array of electronic sensors. The array of electronic sensors is arranged in rows and columns. The second subset of the array of electronic sensors includes a column of electronic sensors. The output of the sensor electrode is in electrical communication with the each electronic sensor within the column of electronic sensors of the second subset of the array of electronic sensors. A reference voltage is provided through a solution in fluid communication with the flow cell in fluid communication with the first subset of the array of electronic sensors. The reference voltage is applied by a reference electrode. The array of electronic sensors includes field effect transistors. The field effect transistors include ion sensitive field effect transistors.

In a related aspect, a solution flows through the sensor electrode. A response of the sensor electrode is measured through the solution. The response of the sensor electrode is amplified. An offset to the measured response of the sensor electrode is provided to center the measured response relative to a reference voltage. The response of the first subset of the array of electronic sensors is adjusted by scaling and subtracting the response of the second subset of the array of electronic sensors.

According to various exemplary embodiments, there is provided a method for correcting nucleotide incorporation signals for fluid potential effects or disturbances arising in nucleic acid sequencing-by-synthesis, comprising: (a) disposing a plurality of template polynucleotide strands in a plurality of defined spaces disposed on a sensor array, at least some of the template polynucleotide strands having a sequencing primer and a polymerase bound therewith; (b) exposing the template polynucleotide strands with the sequencing primer and a polymerase bound therewith to a series of flows of nucleotide species flowed according to a predetermined ordering through a fluid manifold, the fluid manifold comprising passages for flowing nucleotide species and a branch passage for flowing a solution not comprising nucleotide species, the branch passage comprising a reference electrode and a sensing electrode; (c) obtaining a plurality of nucleotide incorporation signals corresponding to the plurality of defined spaces, the nucleotide incorporation signals having a signal intensity related to a number of nucleotide incorporations having occurred in the corresponding defined space; and (d) correcting at least some of the plurality of nucleotide incorporation signals for fluid potential effects or disturbances using a mathematical transformation comprising a scale factor determined based on signals obtained from the sensing electrode for each of a plurality of regions of defined spaces on the sensor array.

According to various exemplary embodiments, there is provided a non-transitory machine-readable storage medium comprising instructions which, when executed and/or implemented by a processor, cause the processor to perform a method for correcting nucleotide incorporation signals for fluid potential effects or disturbances arising in nucleic acid sequencing-by-synthesis comprising: (a) exposing a plurality of template polynucleotide strands disposed in a plurality of defined spaces disposed on a sensor array and having a sequencing primer and a polymerase bound therewith to a series of flows of nucleotide species flowed according to a predetermined ordering through a fluid manifold, the fluid manifold comprising passages for flowing nucleotide species and a branch passage for flowing a solution not comprising nucleotide species, the branch passage comprising a reference electrode and a sensing electrode; (b) obtaining a plurality of nucleotide incorporation signals corresponding to the plurality of defined spaces, the nucleotide incorporation signals having a signal intensity related to a number of nucleotide incorporations having occurred in the corresponding defined space; and (c) correcting at least some of the plurality of nucleotide incorporation signals for fluid potential effects or disturbances using a mathematical transformation comprising a scale factor determined based on signals obtained from the sensing electrode for each of a plurality of regions of defined spaces on the sensor array.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the scope of disclosed embodiments, as set forth by the claims.

BRIEF DESCRIPTION OF THE DRAWINGS

The accompanying drawings, which are incorporated into and form a part of the specification, illustrate one or more exemplary embodiments and serve to explain the principles of various exemplary embodiments. The drawings are exemplary and explanatory only and are not to be construed as limiting or restrictive in any way.

DETAILED DESCRIPTION OF EMBODIMENTS

The following description and the various embodiments described herein are exemplary and explanatory only and are not to be construed as limiting or restrictive in any way. Other embodiments, features, objects, and advantages of the present teachings will be apparent from the description and accompanying drawings, and from the claims.

In this application, "defined space" generally refers to any space (which may be in one, two, or three dimensions) in which at least some of a molecule, fluid, and/or solid can be confined, retained and/or localized. The space may be a predetermined area (which may be a flat area) or volume, and may be defined, for example, by a depression or a micro-machined well in or associated with a microwell plate, microtiter plate, microplate, or a chip, or by isolated hydrophobic areas on a generally hydrophobic surface. Defined spaces may be arranged as an array, which may be a substantially planar one-dimensional or two-dimensional arrangement of elements such as sensors or wells. Defined spaces, whether arranged as an array or in some other configuration, may be in electrical communication with at least one sensor to allow detection or measurement of one or more detectable or measurable parameters or characteristics. The sensors may convert changes in the presence, concentration, or amounts of reaction by-products (or changes in ionic character of reactants) into an output signal, which may be registered electronically, for example, as a change in a voltage level or a current level which, in turn, may be processed to extract information or signal about a chemical reaction or desired association event, for example, a nucleotide incorporation event and/or a related ion concentration (e.g., a pH measurement). The sensors may include at least one ion sensitive field effect transistor ("ISFET") or chemically sensitive field effect transistor ("chemFET"). Defined spaces may sometimes be referred to as reaction confinement areas, which may in an example represent microwells in a semiconductor chip.

Figure 1:
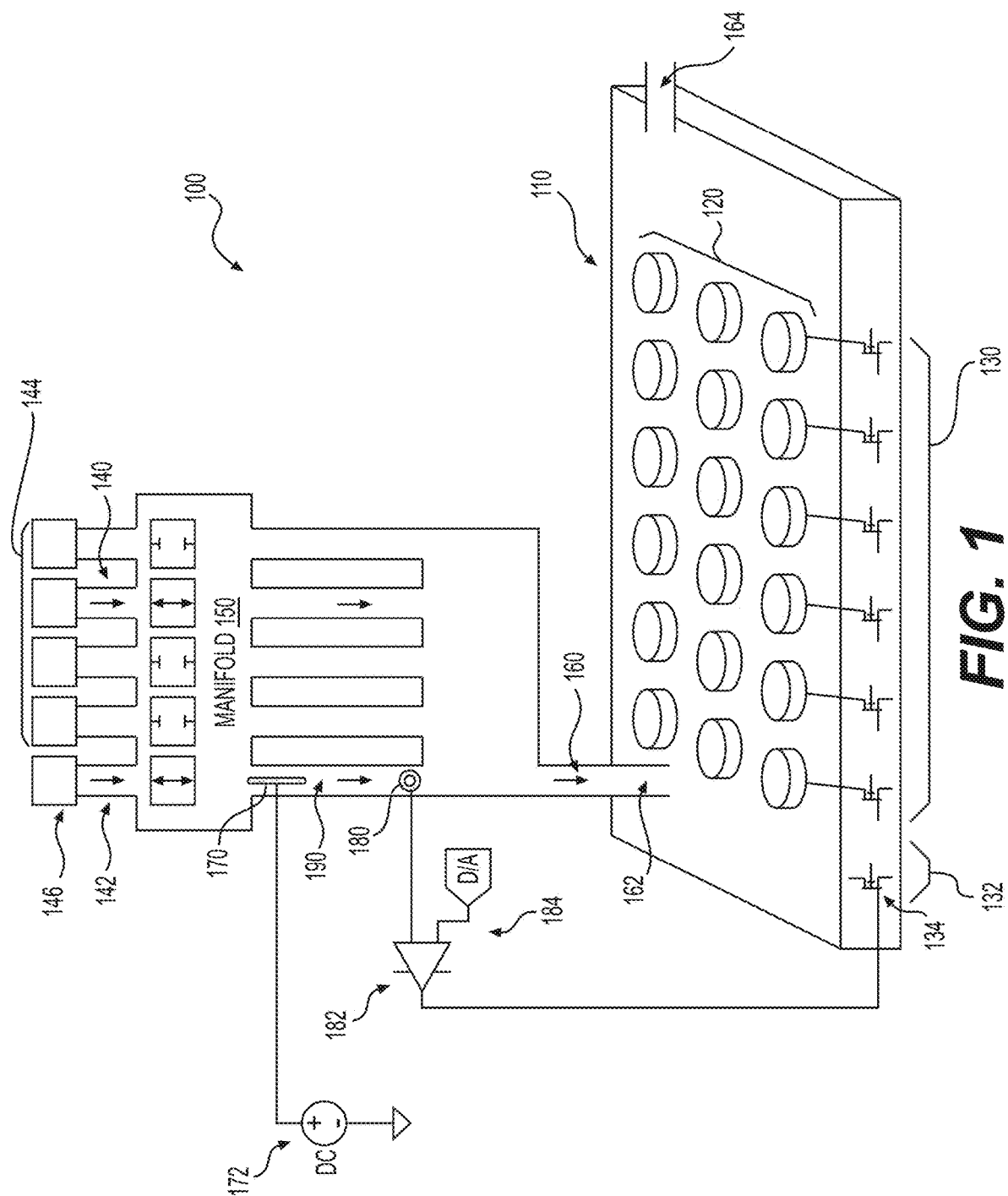
FIG. 1 illustrates a schematic view of an example of an apparatus for delivering reagents to reaction confinement areas, according to exemplary embodiments of the present disclosure.

FIG. 1 illustrates a schematic view of an example of an apparatus for delivering reagents to reaction confinement areas. The apparatus 100 may include a solution reservoir 146, which may include a solution 142 (which may be a wash solution); a plurality of reagent reservoirs 144, which may include a plurality of corresponding reagents 140; a fluid manifold 150, which may be in fluidic communication with the solution reservoir 146 and the plurality of reagent reservoirs 144; a branch passage 190, which may be in fluidic communication with the fluid manifold 150; an outlet passage 160, which may be in fluidic communication with the branch passage 190 and the fluid manifold 150; and a flow cell 110, which may be in fluidic communication with the outlet passage 160 and may be a semiconductor chip. The fluid manifold 150 may include a reference electrode 170, which may provide a reference voltage 172, and a sensor electrode 180 (provided downstream of the reference electrode 170, that is, closer to the outlet passage 160 than the reference electrode 170), which may be coupled to an amplifier 182 providing a reference voltage offset 184 to an output of the sensor electrode 180. The reference electrode 170 and the sensor electrode 180 may contact fluid (such as the solution 142) flowing within the branch passage 190, and reference electrode 170 and sensor electrode 180 may be free of direct contact with any of the reagents 140 that may be flowing through the outlet passage 160.

The flow cell 110 may include a plurality of reaction confinement areas 120 cooperatively engaged with a first array of electronic sensors 130 in fluidic communication with the fluid in the reaction confinement areas 120. As discussed in detail below with regard to FIG. 2, each reaction confinement area 120 has a corresponding electronic sensor 130. The flow cell 110 may also include a second array of electronic sensors 132 not in fluidic communication with the fluid in the reaction confinement areas 120.

The first and second arrays of electronic sensors 130 and 132 may be field-effect transistors having gate electrodes, which may include ISFETs or chemFETs. Each electronic sensor 132 of the second array of electronic sensors 132 may include a gate electrode 134 in electrical communication with the sensor electrode 180. In an example, the amplifier 182 may be in electrical communication between the output of the sensor electrode 180 and the gate electrode 134 of field-effect transistors of the second array of electronic sensors 132.

As shown in FIG. 1, the flow cell 110 may include a fluid inlet 162 in fluidic communication with the outlet passage 160, and a fluid outlet 164 in fluidic communication with the flow cell 110. The sensor electrode 180 may be in electrical communication with the first array of electronic sensors 130 through fluid via the fluid inlet 162 or the fluid outlet 164. As will be discussed below with FIG. 2, the first and second arrays of electronic sensors 130 and 132 may be arranged in rows and columns such that the second array of electronic sensors 132 includes a column of electronic sensors, and each sensor in the column may be in electrical communication with the output of the sensor electrode 180 through a solution via the outlet passage 160.

Figure 2:
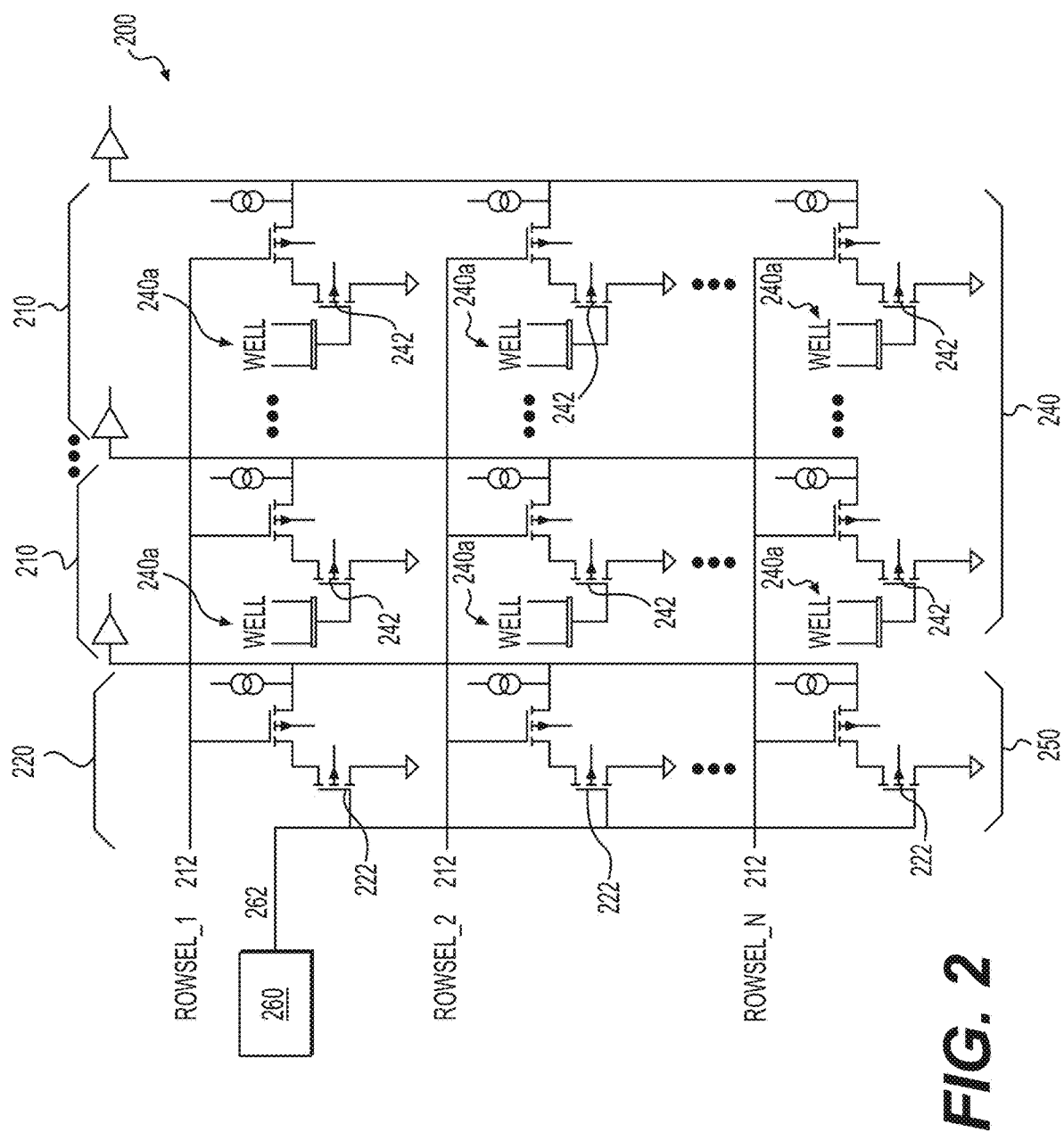
FIG. 2 illustrates an electrical diagram of an example of a sensor array, according to exemplary embodiments of the present disclosure.

FIG. 2 illustrates an electrical diagram of an example of a sensor array. The sensor array 200 may include a plurality of electronic sensors 210 and 220. A first subset 240 of electronic sensors may include the plurality of electronic sensors 210 (see, for example, the second and third column from the left of FIG. 2), which may be exposed to one or more fluids (such as a wash solution or reagents) via fluid access to corresponding reaction confinement areas 240a. A second subset 250 of electronic sensors may include the plurality of electronic sensors 220 (see, for example, the first column from the left of FIG. 2), which may be free of contact with any fluid within the reaction confinement areas 240a.

In an embodiment of the present disclosure, each electronic sensor 210 may include a corresponding reaction confinement area 240a (also referred to as a well 240a), and a field-effect transistor, which may include ISFETS having a gate electrode 242. The reaction confinement areas 240a of FIG. 2 may correspond to the reaction confinement areas 120 of FIG. 1, and the electronic sensors 210 of FIG. 2 may correspond to the electronic sensors 130 of FIG. 1.

Each electronic sensor 220 may include a corresponding field-effect transistor, which may include ISFETS having a gate electrode 222. The electronic sensors 220 of FIG. 2 may correspond to the electronic sensors 132 of FIG. 1. Further, the gate electrode 134 of field-effect transistors of the second array of electronic sensors 132 of FIG. 1 may correspond to the gate electrode 222 of field-effect transistors of the electronic sensors 220.

A sensor electrode 260 may be in electrical communication with the first subset 240 of electronic sensors through fluid in the reaction confinement areas 240a. A sensor electrode output 262 may be in electrical communication with the gate electrodes 222 of the second subset 250 of electronic sensors. The sensor electrode 260 of FIG. 2 may correspond to the sensor electrode 180 of FIG. 1.

As shown in FIG. 2, the sensor array 200 may be arranged in rows and columns such that the second subset 250 of sensors includes a column of electronic sensors 220, which may be in electrical communication with the sensor electrode output 262. The sensor electrode output 262 may be sampled and measured by the second subset 250 of sensors in the same manner the reaction confinement area 240a signals may be sampled and measured by the first subset 240 of sensors.

A row select switch (not shown) may be connected to one through N row select switch lines 212 (see, for example, ROWSEL_1, ROWSEL_2, . . . , ROWSEL_N of FIG. 2), where N is a number of rows of electronic sensors of sensory array 200. The row select switch may be used to select one or more rows of electronic sensors 210 and 220 of the sensor array 200. The selecting of one or more rows of electronic sensors 210 and 220 of the sensory array 200, however, may lead to an undesirable coupling of signals into fluid via capacitance of column metallization.

In an embodiment, the measured response from of an electronic sensor 220 of the second subset 250 in a row with a plurality of electronic sensors 210 of the first subset 240 may be used to adjust the measured response of the electronic sensors 210 within the same row. For example, the response of the first subset 240 of electronic sensors 210 may be adjusted by scaling and subtracting the response of the corresponding second subset 250 of electronic sensors 220 for each selected row.

Figure 3:
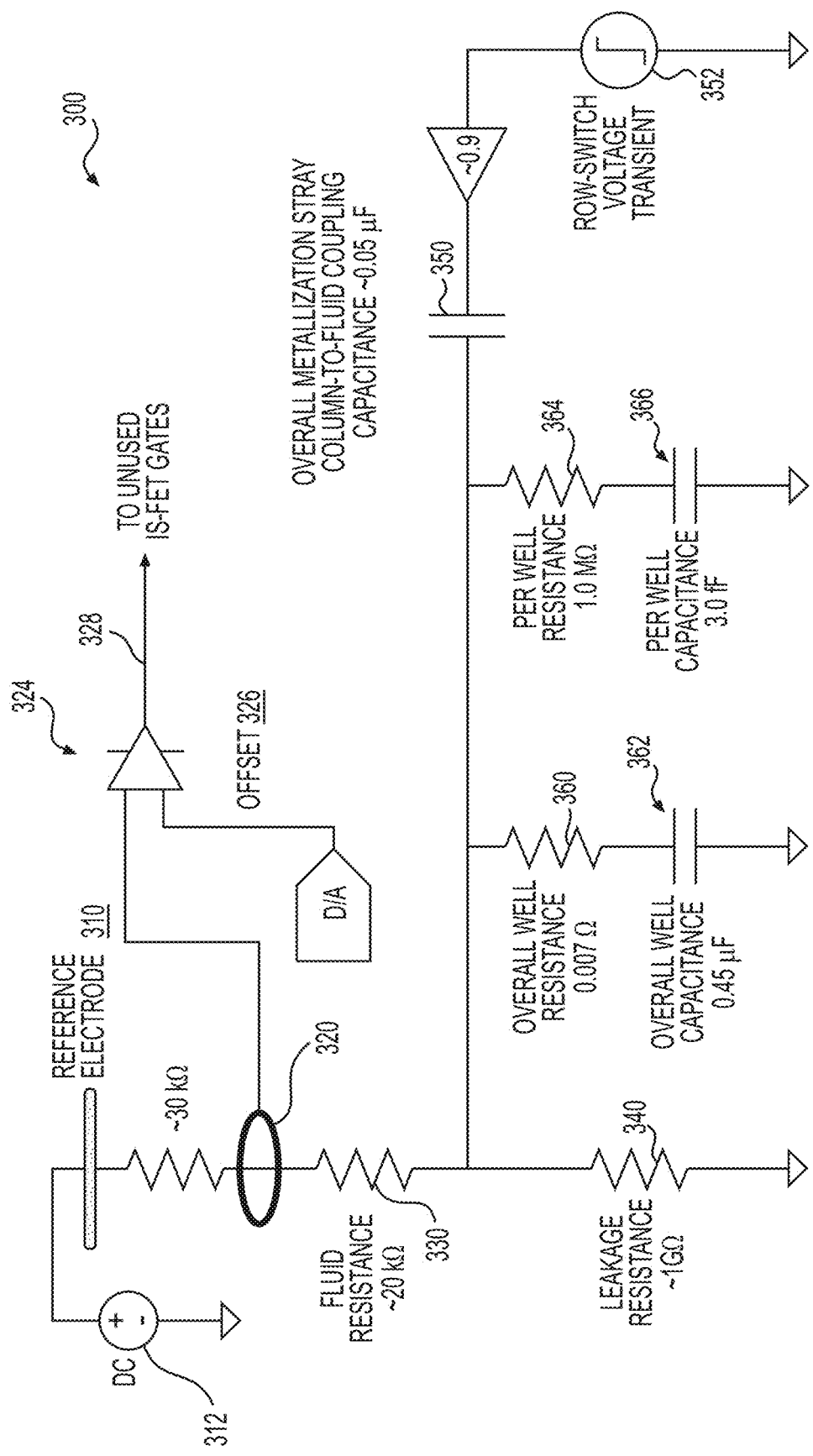
FIG. 3 illustrates an electrical diagram of an example of an electronic sensor, according to exemplary embodiments of the present disclosure.

FIG. 3 illustrates an electrical diagram of an example of an electronic sensor 300. Shown are various resistances and/or capacitances that may introduce error into measurements of the electronic sensor 300. A reference electrode 310 (which may correspond to the reference electrode 170 of FIG. 1) may provide a bias voltage 312 (which may correspond to reference voltage 172 of FIG. 1) for a sensor array, such as sensor array 200 of FIG. 2.

A sensor electrode 320 (which may correspond to sensor electrode 180 of FIG. 1) may output a measured response to an amplifier 324 (which may correspond to amplifier 182 of FIG. 1). A reference voltage offset 326 may be provided to the amplifier 324 and may be an offset to the measured response of the sensor electrode 320 to center the measured response relative to the reference voltage 312. The amplifier output 328 may then be provided to unused, non-well electronic sensors (such as, e.g., the second subset 250 of electronic sensors 220, which are not in contact with fluid described in FIG. 2).

Sources of error, as depicted in FIG. 3, may include: fluid resistance 330, leakage resistance 340, overall metallization stray column-to-fluid coupling capacitance 350, row-switch voltage transient 352, overall well resistance 360, overall well capacitance 362, per-well resistance 364, and per-well capacitance 366. In addition, an electrostatic discharge ("ESD"), which may result from touching of fluid tubes, human contact, etc., may undesirably couple into the fluid and cause measurement disruption. While FIG. 3 depicts example resistances and/or capacitances, these resistances and/or capacitances are not limited to such depicted values.

Measurement Operation

Exemplary operation of an apparatus and sensory array, as illustrated in FIGS. 1 and 2, will now be described in detail.

In an embodiment, a reagent 140, such as from one of the reagent reservoirs 144 of the plurality of reagent reservoirs 144, may flow via the fluid manifold 150 into a flow cell 110 having a sensory array, such as sensor array 200 of FIG. 2. The reagent 140 may react to provide a reaction product within one or more of the plurality of reaction confinement areas 120 of FIG. 1 or the one or more of the plurality of reaction confinement areas 240a of FIG. 2.

A solution 142, such as from the solution reservoir 14, may also flow via the fluid manifold 150 and branch passage 190 (which may include the reference electrode 170 and the sensor electrode 180 of FIG. 1). The reference electrode 170 may apply the reference voltage 172 through the solution 142, which is in fluidic communication with the flow cell 110 having the sensory array, such as sensor array 200 of FIG. 2, and with the first array of electronic sensors 130 (the plurality of electronic sensors 210 of the first subset 240 of FIG. 2). A response (e.g., voltage) of the sensor electrode 180 (sensor electrode 260 of FIG. 2) may be measured through the solution 142 and may be amplified by the amplifier 182 providing the reference voltage offset 184.

In the flow cell 110 having the sensor array, such as sensor array 200, a first array of electronic sensors 130 (the plurality of electronic sensors 210 of the first subset 240 of FIG. 2) may measure a response (e.g., voltage) to the reaction product, and a second array of electronic sensors 132 (the plurality of electronic sensors 220 of the second subset 250 of FIG. 2), which may be in electrical communication with the sensor electrode 180 (sensor electrode 260 of FIG. 2) but may not be in fluid communication with the plurality of reaction confinement areas 120 (reaction confinement areas 240a of FIG. 2). An output of the amplifier 182 may be provided as an input to the second array of electronic sensors 132 (i.e., to the sensor electrode output 262 connected to the plurality of electronic sensors 220 of the second subset 250). The output of the amplifier 182 may be used to center the measured response relative to the reference voltage 172. The response of the first array of electronic sensors 130 (the electronic sensors 210 of FIG. 2) may be adjusted by scaling and subtracting the response of the second array of electronic sensors 132 (the electronic sensors 220 of FIG. 2).

As discussed above, the first array of electronic sensors 130 (the first subset 240 of electronic sensors 210 of FIG. 2) and the second array of electronic sensors 132 (the second subset 250 of electronic sensors 220 of FIG. 2) may represent an array of electronic sensors arranged in rows and columns. For example, the first array of electronic sensors 130 may include a first subset 240 of electronic sensors 210 (see, for example, the second and third column from the left of FIG. 2) exposed to the reagent solution 140 within the a flow cell 110 having a sensor array, such as the sensor array 200. The second array of electronic sensors 132 may include a second subset 250 of electronic sensors 220 (see, for example, the first column from the left of FIG. 2).

The output of the sensor electrode 180 (sensor electrode 260 of FIG. 2) may be in electrical communication with each electronic sensor 132 (each electronic sensor 220 of FIG. 2 within the column of electronic sensors 220 of the second subset 250. The second subset 250 of electronic sensors 220 may be free of contact with the reagent solution fluid 140 within the flow cell 120 having the sensor array (sensor array 200) and may instead be in electrical contact with the output of the sensor-electrode amplifier (182) output 260.

Figure 4:
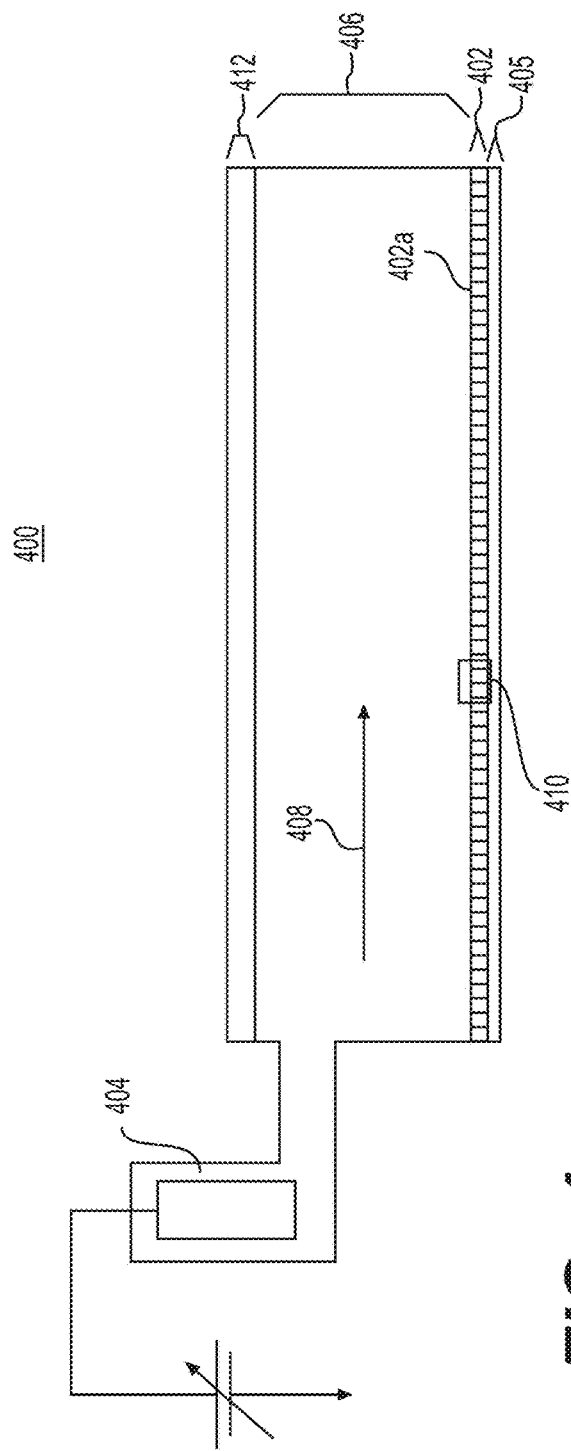
FIG. 4 illustrates an expanded and cross-sectional view of an example flow cell and a portion of an example flow chamber, according to exemplary embodiments of the present disclosure.

In an example embodiment, a sequencing system may include a flow cell having a sensory array, communication circuitry in electronic communication with the sensory array, and containers and fluid controls in fluidic communication with the flow cell. FIG. 4 illustrates an expanded and cross-sectional view of a flow cell 400 and illustrates a portion of a flow chamber 406. A reagent 408, such as a reagent 140 from one of the plurality of reagent reservoirs 144, may flow across a surface 402a of a well array 402. For example, the reagent 408 may flow over the open ends of a plurality of wells of the well array 402. A sensor array 405 may be disposed adjacent to the well array 402, and the sensory array 405 and the well array 402 may together form an integrated unit forming a lower wall (or floor) of the flow cell 400. A reference electrode 404 may be fluidically coupled to flow chamber 406. Further, a flow cell cover 412 may encapsulate flow chamber 406 to contain reagent 408 within a confined region.

Figure 5:
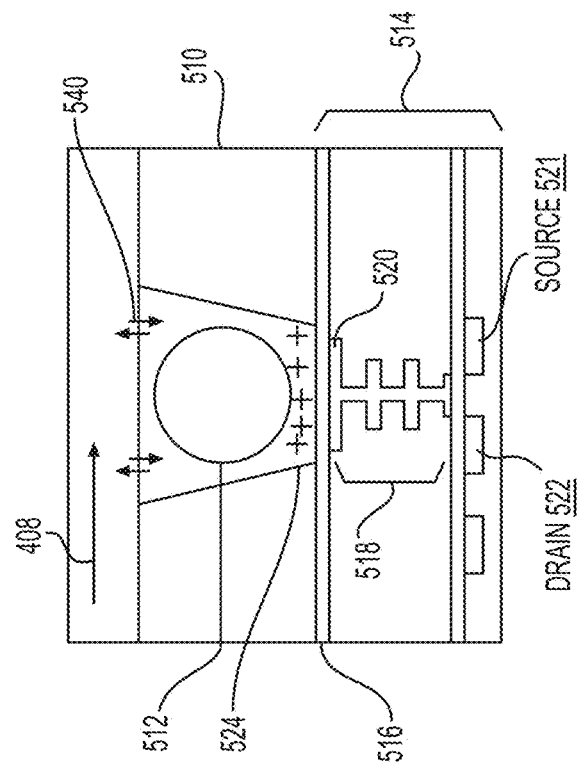
FIG. 5 illustrates an expanded view of an example well and an example sensor, according to exemplary embodiments of the present disclosure.

FIG. 5 illustrates an expanded view of a well 510 and a sensor 514, such as a well of the well array 402 and a sensor of the sensor array 405, as illustrated at 410 of FIG. 4. The volume, shape, aspect ratio (such as base width-to-well depth ratio), and other dimensional characteristics of the wells may be selected based on the nature of the reaction taking place, as well as the reagents, byproducts, or labeling techniques (if any) that may be employed.

The sensor 514 of the sensor array may be a a field-effect transistor ("FET"), such as a chemFET, or, for example, more specifically an ISFET. The field-effect transistor may have a floating gate 518 including a sensor plate 520. The floating gate 518 of the field-effect transitory may optionally separated from an interior area of the well 510 by a material layer 516. In addition, a conductive layer (not illustrated) may be disposed over the sensor plate 520. In an example, the material layer 516 may include an ion sensitive material layer. The material layer 516 may be a ceramic layer, such as an oxide of zirconium, hafnium, tantalum, aluminum, or titanium, among others, or a nitride of titanium. Alternatively, the material layer 516 may be formed of a metal, such as titanium, tungsten, gold, silver, platinum, aluminum, copper, or a combination thereof. In an example, the material layer 516 may have a thickness in a range of 5 nm to 100 nm+/−15%, such as a range of 10 nm to 70 nm, a range of 15 nm to 65 nm, or even a range of 20 nm to 50 nm.

While the material layer 516 is illustrated as extending beyond the bounds of the illustrated FET component, the material layer 516 may extend along the bottom of the well 510, and the material layer 516 may optionally extend along the walls of the well 510. The sensor 514 may be responsive to (and may generate an output signal related to) the amount of a charge 524 present on the well 510 side of the material layer 516 that opposes the sensor plate 520 side of the sensor 514.

Changes in the charge 524 may cause changes in a current between a source 521 and a drain 522 of the FET. In turn, the FET of the sensor 514 may be used directly to provide a current-based output signal and/or indirectly with additional circuitry to provide a voltage-based output signal. Reactants, wash solutions, and other reagents may move in and out of the well 510 by a diffusion mechanism 540.

In one embodiment, reactions carried out in the well 510 may be analytical reactions to identify or determine characteristics or properties of an analyte of interest. Such reactions may generate directly or indirectly byproducts that affect the amount of charge adjacent to the sensor plate 520. If such byproducts are produced in small amounts, rapidly decay, and/or react with other constituents, multiple copies of the same analyte may be analyzed in the well 510 at the same time in order to increase the output signal generated.

In an embodiment of the present disclosure, multiple copies of an analyte may be attached to a solid phase support 512, either before or after deposition into the well 510. The solid phase support 512 may be a polymer matrix, such as a hydrophilic polymer matrix, for example, a hydrogel matrix or the like. For simplicity and ease of explanation, the solid phase support 512 may also be referred herein as a polymer matrix.

The well 510 may be defined by a wall structure, which may be formed of one or more layers of material. In one embodiment, the wall structure may have a thickness extending from the lower surface to the upper surface of the well in a range of 0.01 micrometers to 10 micrometers+/−15%, such as a range of 0.05 micrometers to 10 micrometers, a range of 0.1 micrometers to 10 micrometers, a range of 0.3 micrometers to 10 micrometers, and/or a range of 0.5 micrometers to 6 micrometers. In a particular embodiment, the thickness may be in a range of 0.01 micrometers to 1 micrometer+/−15%, such as a range of 0.05 micrometers to 0.5 micrometers, or a range of 0.05 micrometers to 0.3 micrometers. The well 510 may have a characteristic diameter, defined as the square root of 4 times the cross-sectional area (A) divided by Pi (e.g., sqrt(4*A/π), of not greater than 5 micrometers, such as not greater than 3.5 micrometers, not greater than 2.0 micrometers, not greater than 1.6 micrometers, not greater than 1.0 micrometers, not greater than 0.8 micrometers or even not greater than 0.6 micrometers. In an example embodiment, the well 510 may have a characteristic diameter of at least 0.01 micrometers+/−15%. In a further example embodiment, the well 510 may define a volume in a range of 0.05 fL to 10 pL+/−15%, such as a volume in a range of 0.05 fL to 1 pL, a range of 0.05 fL to 100 fL, a range of 0.05 fL to 10 fL, or even a range of 0.1 fL to 5 fL.

While FIG. 5 illustrates a single-layer wall structure and a single-layer material layer 516, the system may include one or more wall structure layers, one or more conductive layers, and/or one or more material layers. For example, the wall structure may be formed of one or more layers, including an oxide of silicon, tetraethyl orthosilicate ("TEOS"), and/or a nitride of silicon.

Nucleic acid beads may be loaded into a biosensor for determining characteristics of the nucleic acid beads. In particular, the nucleic acid beads may be used for sequence target sequences conjugated to the nucleic acid beads. For example, sequencing may include label-free DNA sequencing, and in particular, pH-based DNA sequencing. Substrates including DNA templates and having a primer and polymerase operably bound may be loaded into reaction confinement areas (such as reaction confinement areas 120 of FIG. 1, reaction confinement areas 240a of FIG. 2, and/or a well 510 of FIG. 5), after which repeated cycles of deoxynucleoside triphosphate ("dNTP") addition and washing may be carried out. Such templates may be attached as clonal populations to the substrate, such as a microparticle, bead, or the like, and such clonal populations may be loaded into reaction confinement areas. In each additional step of the cycle, the polymerase may extend the primer by incorporating added dNTP when the next base in the template is the complement of the added dNTP.

When there is one complementary base, there may be one incorporation, when two, there may be two incorporations, when three, there may be three incorporations, and so on. With each such incorporation there may be a hydrogen ion released, and collectively a population of templates releasing hydrogen ions may cause very slight changes in the local pH of the reaction confinement area, which may be detected by an electronic sensor (such as sensor 514 of FIG. 5).

Figure 6:
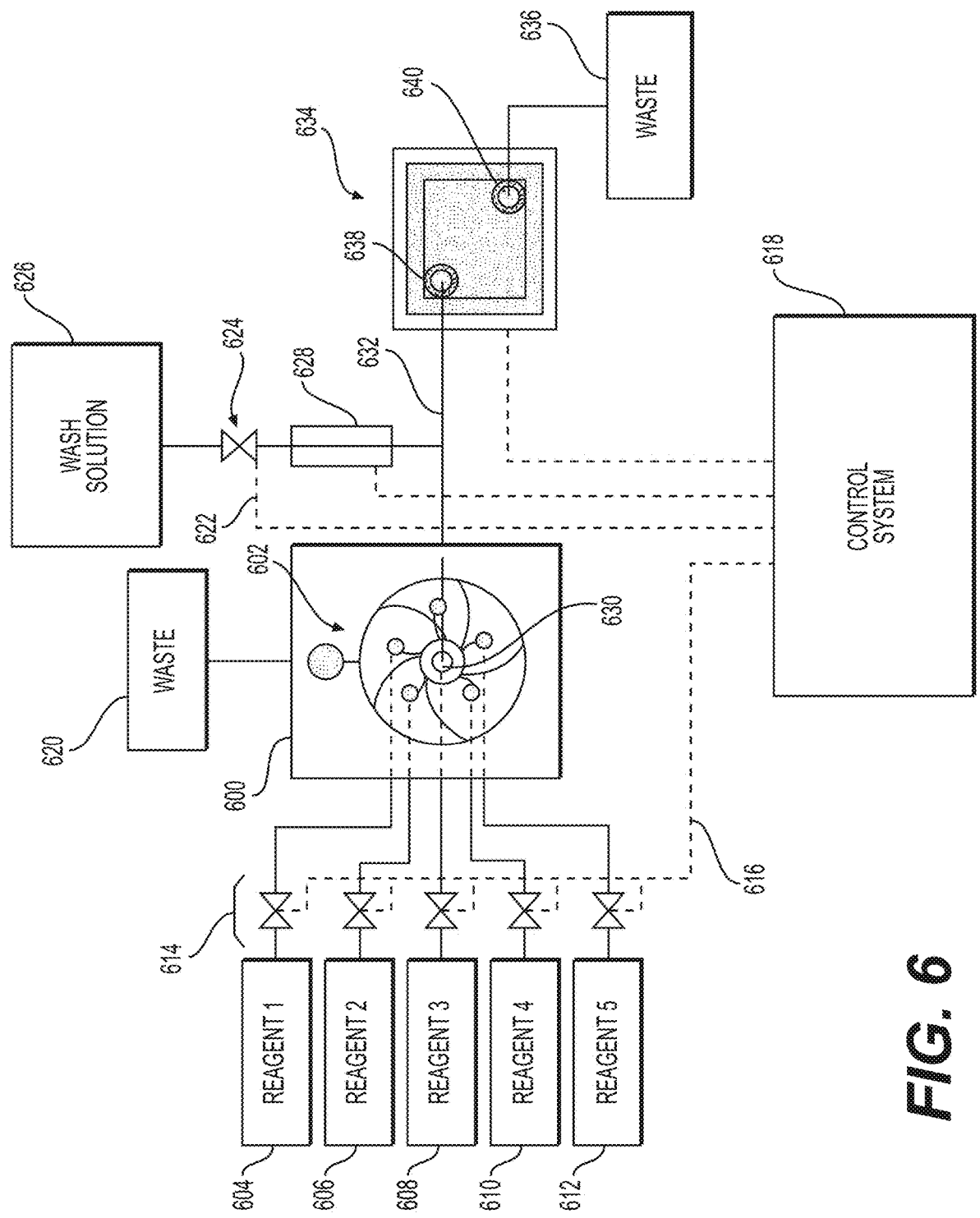
FIG. 6 diagrammatically illustrates an example apparatus for carrying out pH-based nucleic acid sequencing, according to exemplary embodiments of the present disclosure.

FIG. 6 diagrammatically illustrates an apparatus for carrying out pH-based nucleic acid sequencing. Each electronic sensor of the apparatus may generate an output signal that depends on the value of a reference voltage. In FIG. 6, a housing 600 may contain fluidics circuit 602 that may be connected by inlets to reagent reservoirs 604, 606, 608, 610, and 612 (such as the plurality of reservoirs 144 of FIG. 1), to waste reservoir 620, and to flow cell 634 (such as flow cell 110 of FIG. 1) by passage 632 that may connect fluidics node 630 to inlet 638 of flow cell 634. Reagents from reservoirs 604, 606, 608, 610, and 612 may be driven to fluidic circuit 602 by a variety of methods including, but not limited to, pressure, pumps, such as syringe pumps, gravity feed, and the like, and may be selected by control of valves 614. Control system 618 may include controllers for valves 614 that generate signals for opening and closing via an electrical connection 616. Control system 618 may also include controllers for other components of the system, such as wash solution valve 624 connected thereto by an electrical connection 622, and reference electrode 628 by an electrical connection.

Control system 618 may also include control and data acquisition functions for flow cell 634. In one mode of operation, fluidics circuit 602 may deliver a sequence of selected reagents (such as reagents 1, 2, 3, 4, and 5) to flow cell 634 under programmed control of control system 618, such that in between selected reagent flows, fluidics circuit 602 may be primed and washed, and flow cell 634 may washed. Fluids entering flow cell 634 may exit through an outlet 640 and may be deposited in a waste container 636. Throughout such an operation, the reactions or measurements taking place in flow cell 634 may have a stable reference voltage because reference electrode 628 has a continuous, i.e. uninterrupted, electrolyte pathway with flow cell 634, but is in physical contact with the wash solution 626.

An exemplary apparatus may include a device including a flow cell in fluid communication with an electronic sensor, a plurality of reagent reservoirs to include a plurality of reagents, a fluid manifold in fluidic communication with the plurality of reagent reservoirs, an outlet passage of the fluid manifold in fluid communication with the flow cell, a reference electrode to provide a reference voltage to the electronic sensor through fluid in the outlet passage and the flow cell, and a sensor electrode in electrical communication with the fluid of the outlet passage and the flow cell. The fluid manifold may further include a branch passage between the fluid manifold and the flow cell in fluid communication with the outlet passage. The reference electrode may be disposed in contact with fluid within the branch passage. The reference electrode may be free of direct contact with any reagent of the plurality of reagents when the any reagent flows through the outlet passage. The sensor electrode may be disposed in contact with fluid within the branch passage. The sensor electrode may be disposed closer to the outlet passage than the reference electrode. The sensor electrode may be free of direct contact with any reagent of the plurality of reagents when the any reagent flows through the outlet passage. The apparatus may further include a solution reservoir in fluid communication with the branch passage. The apparatus as in any one of the preceding examples may further include a second electronic sensor not in fluid communication with the flow cell, the second electronic sensor including a gate electrode, and an output from the sensor electrode in electrical communication with the gate electrode. The apparatus as in any one of the preceding examples may further include an amplifier coupled to the sensor electrode and providing a reference voltage offset to the sensor electrode. The apparatus as in any one of the preceding examples may further include an electronic sensor including a field effect transistor including a gate electrode. The apparatus as in any one of the preceding examples may further include an electronic sensor including an ion sensitive field effect transistor.

Another exemplary apparatus may include a flow cell including a fluid inlet and a fluid outlet, an array of electronic sensors cooperatively engaged with the flow cell, each of the electronic sensors including a field effect transistor including a gate electrode, a first subset of the array of electronic sensors exposed to a fluid within the flow cell, a second subset of the array of electronic sensors free of contact with the fluid within the flow cell, and a sensor electrode in electrical communication with the first subset of the array of electronic sensors through fluid via the fluid inlet or the fluid outlet, an output of the sensor electrode in electrical communication with the gate electrodes of the field effect transistors of the second subset of the array of electronic sensors. The array of electronic sensors may be arranged in rows and columns, wherein the second subset of the array of electronic sensors includes a column of electronic sensors, the output of the sensor electrode in electrical communication with the each electronic sensor within the column of electronic sensors of the second subset of the array of electronic sensors. The apparatus may further include a fluid manifold in fluid communication with a plurality of reagent reservoirs, the fluid manifold including an outlet passage in fluid communication with the fluid inlet, the sensor electrode in electrical communication with the second subset of the array of electronic sensors through a solution via the outlet passage. The apparatus may further include a branch passage between the fluid manifold and the flow cell in fluid communication with the outlet passage, the sensor electrode disposed in the branch passage. The reference electrode may be disposed in contact with fluid within the branch passage. The reference electrode may be free of direct contact with any reagent of the plurality of reagents when the any reagent flows through the outlet passage. The sensor electrode may be disposed in contact with fluid within the branch passage. The sensor electrode may be disposed closer to the outlet passage than the reference electrode. The sensor electrode may be free of direct contact with any reagent of the plurality of reagents when the any reagent flows through the outlet passage. The apparatus may further include a solution reservoir in fluid communication with the branch passage. The plurality of reagent reservoirs may include a plurality of reagents. The apparatus as in any one of the preceding examples may further include a reference electrode to provide a reference voltage to the first subset of the array of electronic sensors through a solution via the fluid inlet or the fluid outlet. The apparatus as in any one of the preceding examples may further include an array of wells providing fluid access to the gate electrodes of the field effect transistors of the first subset of the array of electronic sensors. The apparatus as in any one of the preceding examples may further include an amplifier disposed in electrical communication between the output of the sensor electrode and the gate electrodes of the field effect transistors of the second subset of the array of electronic sensors. The apparatus as in any one of the preceding examples may further include the field effect transistors of the first subset of the array of electronic sensors including ion sensitive field effect transistors.

An exemplary method of measuring a reaction product includes flowing a reagent solution into a flow cell, the reagent solution reacting to provide a reaction product, the flow cell in fluid communication with a first electronic sensor, measuring a response of the first electronic sensor to the reaction product, measuring a response of a second electronic sensor, the second electronic sensor in electrical communication with a sensor electrode in fluid communication with the flow cell, the second electronic sensor not in fluid communication with the flow cell, and adjusting the response of the first electronic sensor based on the response of the second electronic sensor. The method may further include applying a reference voltage through a solution in fluid communication with the flow cell in fluid communication with the first electronic sensor. The reference voltage is applied by a reference electrode. The first electronic sensor and the second electronic sensor include field effect transistors. The field effect transistor of the first electronic sensor may include an ion sensitive field effect transistor. The method may further include flowing a solution through the sensor electrode, measuring a response of the sensor electrode through the solution, and amplifying the response of the sensor electrode. The method may further include providing an offset to the measured response of the sensor electrode to center the measured response relative to a reference voltage. The method as in any one of the preceding examples may include the response of the first electronic sensor being adjusted by scaling and subtracting the response of the second electronic sensor.

Another exemplary method of measuring a reaction product includes flowing a reagent solution into a flow cell, the reagent solution reacting to provide a reaction product, the flow cell in fluid communication with an array of electronic sensors cooperatively engaged with the flow cell, a first subset of the array of electronic sensors exposed to the reagent solution within the flow cell, a second subset of the array of electronic sensors free of contact with the reagent solution fluid within the flow cell, measuring a response of the first subset of the array of electronic sensors to the reaction product, measuring a response of the second subset of the array of electronic sensors, the second subset of the array of electronic sensors in electrical communication with a sensor electrode in fluid communication with the flow cell, and adjusting the response of the first subset of the array of electronic sensors based on the response of the second subset of the array of electronic sensors. The method may include each of the electronic sensors including a field effect transistor including a gate electrode, and the sensor electrode in electrical communication with the first subset of the array of electronic sensors through fluid, an output of the sensor electrode in electrical communication with the gate electrodes of the field effect transistors of the second subset of the array of electronic sensors. The method may include the array of electronic sensors being arranged in rows and columns, wherein the second subset of the array of electronic sensors includes a column of electronic sensors, the output of the sensor electrode in electrical communication with the each electronic sensor within the column of electronic sensors of the second subset of the array of electronic sensors. The method may further include applying a reference voltage through a solution in fluid communication with the flow cell in fluid communication with the first subset of the array of electronic sensors. The method may include the reference voltage being applied by a reference electrode. The method may include the array of electronic sensors including field effect transistors. The method may include field effect transistors including ion sensitive field effect transistors. The method as in any one of the preceding examples may further include flowing a solution through the sensor electrode, measuring a response of the sensor electrode through the solution, and amplifying the response of the sensor electrode. The method as in any one of the preceding examples may further include providing an offset to the measured response of the sensor electrode to center the measured response relative to a reference voltage. The method as in any one of the preceding examples may include the response of the first subset of the array of electronic sensors being adjusted by scaling and subtracting the response of the second subset of the array of electronic sensors.

Sensing Electrode Data

Figure 7A:
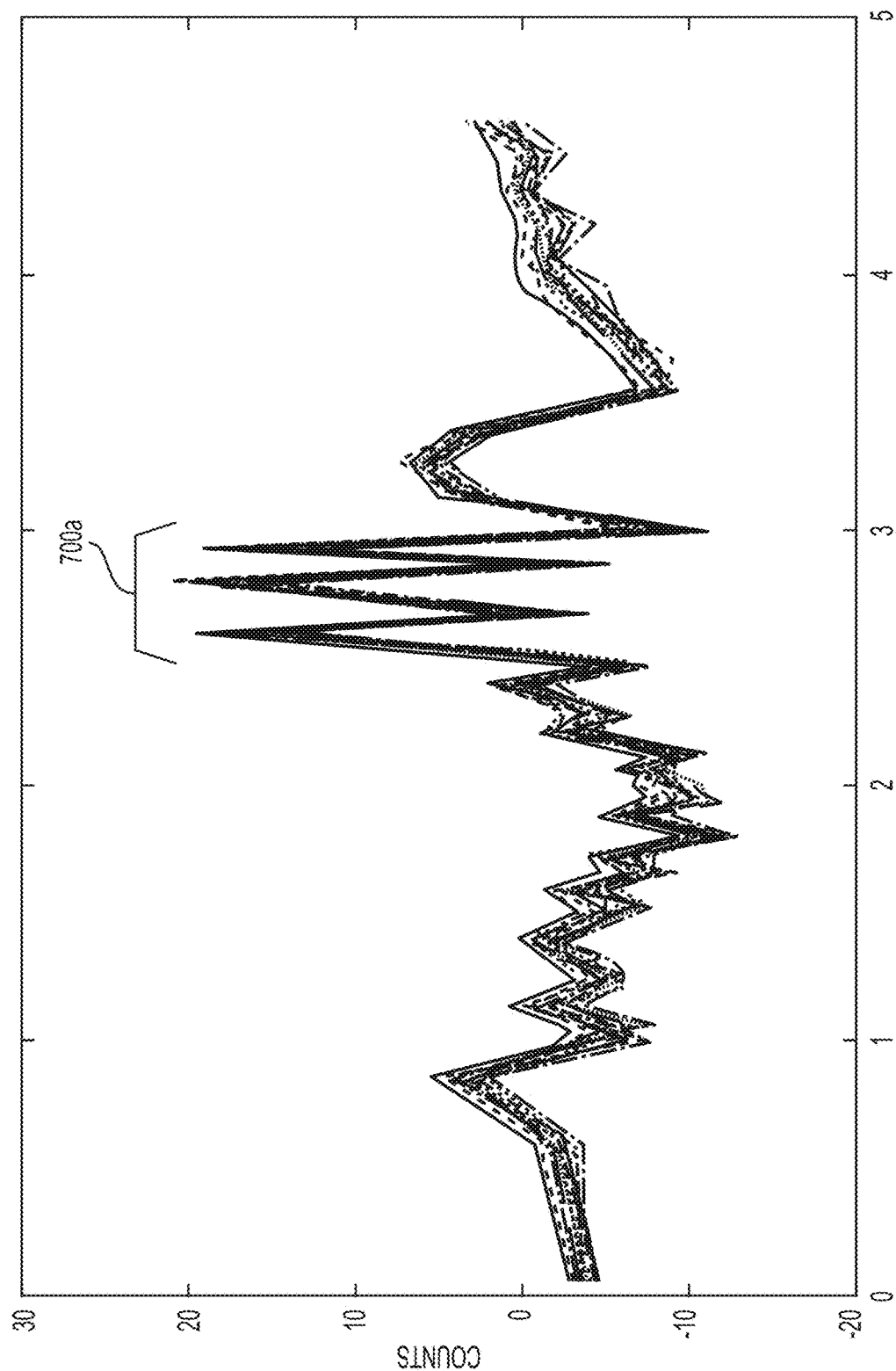
FIG. 7A illustrates an example of sensing electrode data, according to exemplary embodiments of the present disclosure.

FIG. 7A illustrates an example of sensing electrode data. In this example, a sensing electrode signal may be sampled at a rate of 30 Hz for each of 100 rows in a region of 100×100 wells in a sample array. The x-axis represents time during sensing, expressed in seconds. The y-axis represents voltage, expressed in counts (which may be for practical purposes proportional to voltage, with 1 count representing 2.5 mV). The sensing electrode signal may be measured in the same way as well signals, and the amplified signal from the sensing electrode may be applied to unused ISFET transistor columns. The sense electrode and well readings may be simultaneous for the same row. As shown in FIG. 7A, the traces for the various rows may be similar, and there may appear to be a relatively clear three-peak electrical disturbance 700a in fluid potential shortly before the three-second mark.

Figure 7B:
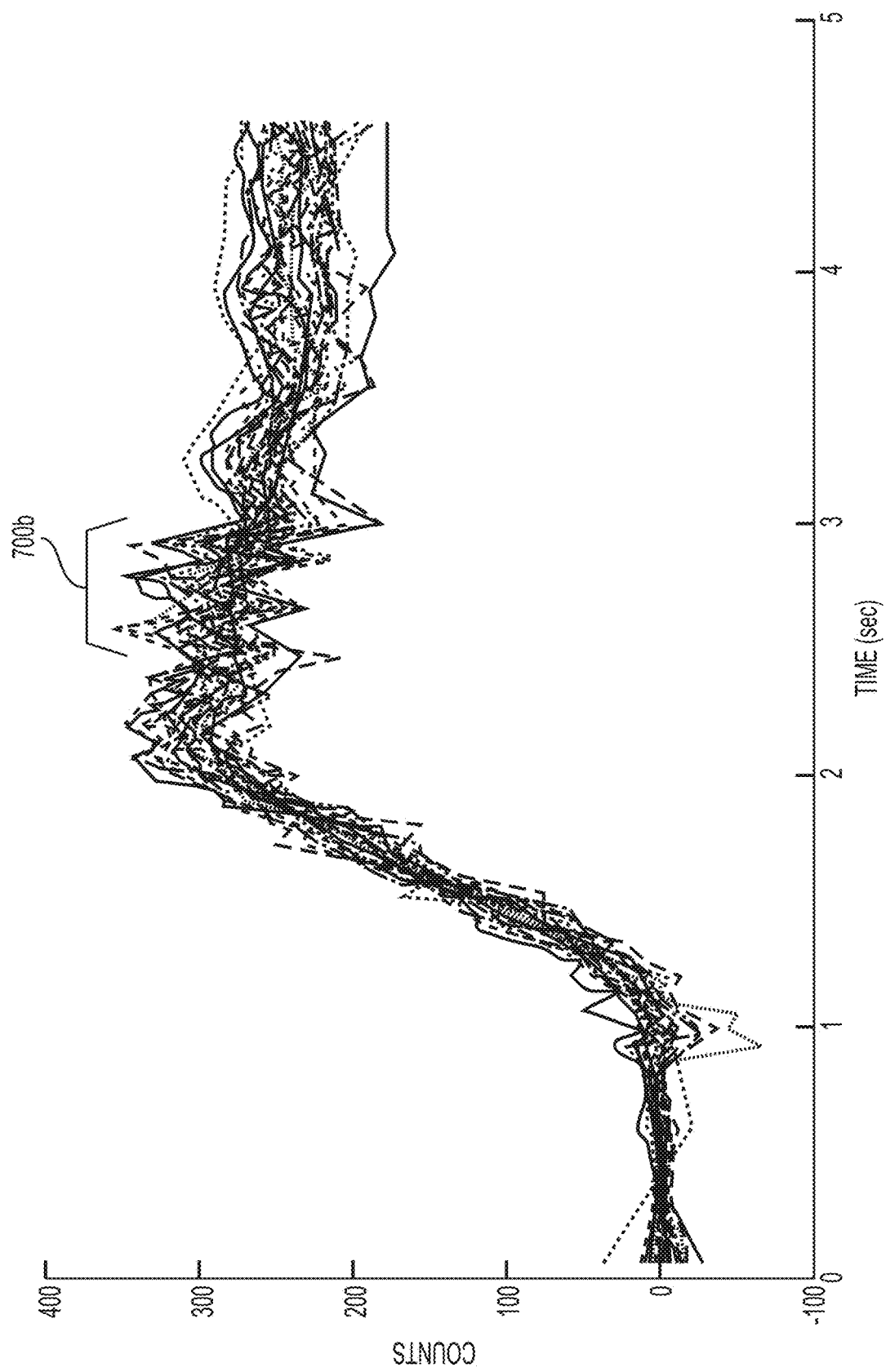
FIG. 7B illustrates an example of electrical disturbance in reaction confinement area data, according to exemplary embodiments of the present disclosure.

FIG. 7B illustrates an example of electrical disturbance in reaction confinement area data. In this example, a reaction confinement area signal may be sampled at a rate of 30 Hz for each well in a region of 100×100 wells comprising ISFETs in contact with fluid in a sample array. The x-axis represents time during sensing, expressed in seconds. The y-axis represents voltage, expressed in counts (which may be for practical purposes proportional to voltage). As shown in FIG. 7B, the traces for the various wells may be similar, and the three-peak electrical disturbance 700a in fluid potential picked-up relatively clearly in the sensing electrode data of FIG. 7A may appear to also be present in the data of FIG. 7B, as three-peak electrical disturbance 700b (albeit less clearly given that the disturbance occurred at a time where the level of counts was much higher than the baseline of around zero or so in FIG. 7A).

In one embodiment, sensing electrode signals acquired simultaneously with the well signal may be used to remove some or all high frequency noise using an appropriate mathematical transformation. In an example, the mathematical transformation may use an expression $w_c(t)=w(t)-\alpha\, s(t)$, where $w_c(t)$ represents a corrected well signal, $w(t)$ represents an initial or uncorrected well signal, $s(t)$ represents a sensing electrode signal, and $\alpha$ represents a scale factor. The scale factor $\alpha$ may be determined or estimated in any suitable way, which may be analytical, model-based, and/or empirical or some combination thereof.

In an example, the scale factor $\alpha$ may be determined as follows: (1) for a fixed $\alpha$, calculate $w_c(t)$ using the above formula for each well in a region of wells (e.g., 100 by 100 wells); (2) calculate the average trace $\overline{w_c}(t)$ to remove non-common-mode noise; (3) fit $\overline{w_c}(t)$ with local polynomials; (4) calculate a mean square error of $\overline{w_c}(t)$ from the fit; and (5) select the optimal scale factor $\alpha$ that minimizes the mean square error. In the above steps, any suitable means for selecting fixed starting point estimates, calculating average traces, fitting functions to polynomials, and calculating mean square errors may be used. Regarding step (1) in particular, any suitable means for selecting fixed starting point estimates may be used, however, preferably a list of values of α may be predetermined from 0 to 10 at 0.2 intervals. Regarding step (3) in particular, any suitable local polynomial may be used, however, preferably the local polynomials may be determined using a digital filter that may be applied to a set of digital data points for the purpose of smoothing the data, that is, to increase the signal-to-noise ratio without greatly distorting the signal. Such a digital filter may be a Savitzky-Golay filter, for example, and further preferably using a $2^{nd}$ order Savitzky-Golay filter and 7 frames. The following document relates to digital filters, such as a Savitzky-Golay filter, and is incorporated by reference herein in its entirety: Savitzky & Golay, "Smoothing and Differentiation of Data by Simplified Least Squares Procedures," Analytical Chemistry, 36(8):1627-39 (1964).

In various embodiments, other filters likely to maintain meaningful transients (e.g., a pH step) while removing most of the high frequency noise (e.g., a median filter, a finite impulse response ("FIR") low pass filter, a FIR Filter, an infinite impulse response ("IIR") low pass filter, an IIR filter, etc.) may be used although such other filters may or may not work as well as a Savitzky-Golay filter.

In an embodiment, a scale factor α determined as described above may be further determined using an additional step as follows: (6) refine the selected optimal scale factor α by applying a quadratic fit to the scale factor α that minimizes the error and its nearest neighbors. For example, if α=5.2 minimizes mean square error with value err(5.2), α values x=5.0, 5.2, and 5.4 and y=err(5.0), err(5.2), and err(5.4) may be used to fit with quadratic equation y=a $x^2$+b x+c. The re-estimated optimal scale factor α may then be given by the minimum as predicted by the quadratic equation, i.e., −b/2a. The advantage of this additional step may be to remove a quantization artifact introduced by the arbitrary interval size of 0.2, while allowing relatively large step size (e.g., 0.2) to improve performance.

In an embodiment, sensing electrode signals acquired simultaneously with the well signal may be used to remove some or all high frequency noise using an appropriate mathematical transformation implemented using a method, system, and/or computer-readable medium, which may include instructions as set forth in the following samples of code, which are exemplary only and not limiting in any way.

An example of source code for removal of some or all high frequency noise using a transformation is provided in a computer program listing appendix as an ASCII text file named LT00942_Computer_Program_Listing.txt, as previously described herein.

Figure 8:
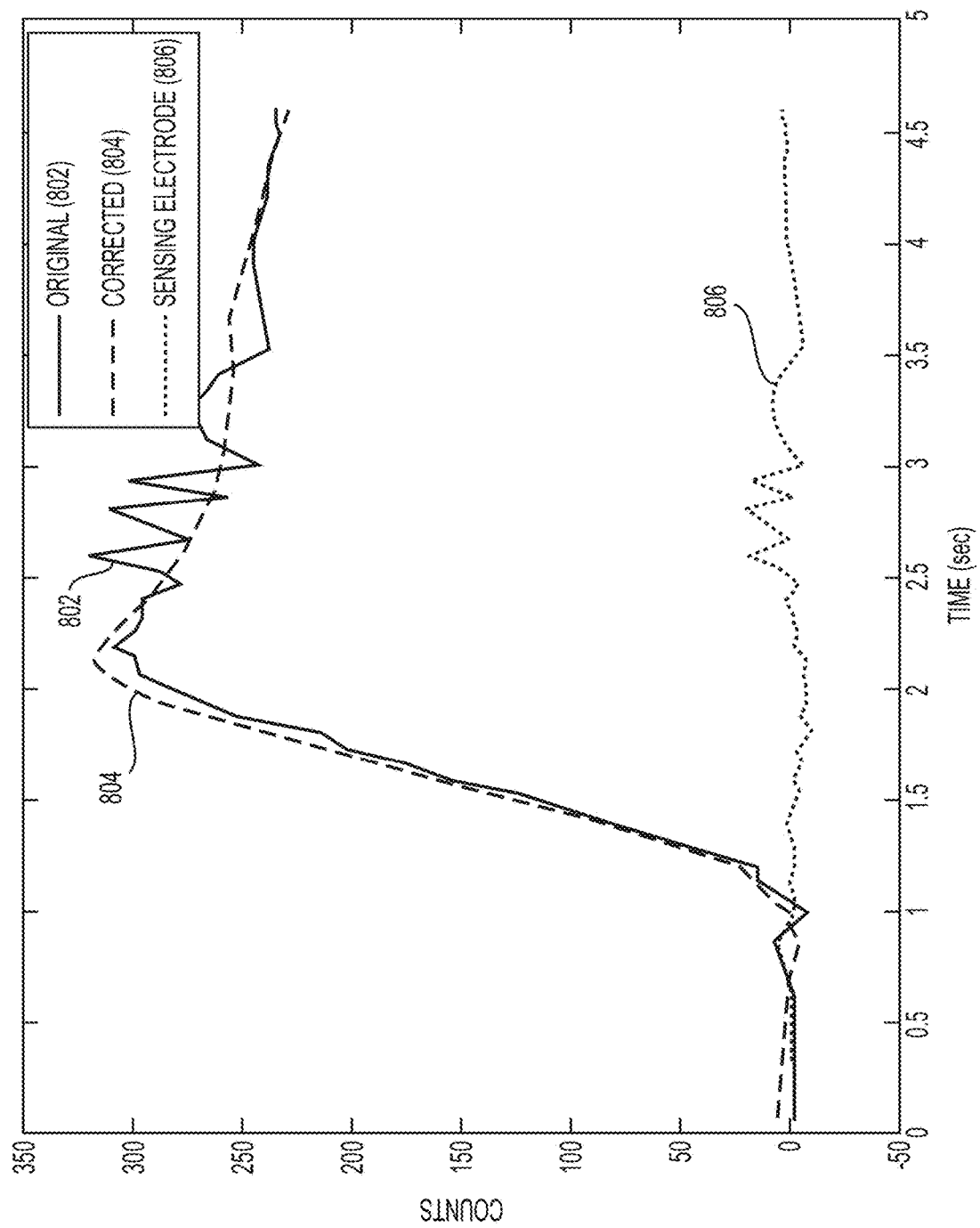
FIG. 8 illustrates an example of fluid potential signal correction, according to exemplary embodiments of the present disclosure.

FIG. 8 illustrates an example of fluid potential signal correction. The x-axis represents time during sensing, expressed in seconds. The y-axis represents voltage, expressed in counts (which may be for practical purposes proportional to voltage). Curve 802 (see top curve with peaks between 2.5 and 3 seconds) depicts an original or uncorrected signal. Curve 804 (see smooth curve without peaks) depicts a corrected signal. Curve 806 (see bottom curve with peaks between 2.5 and 3 seconds) depicts the sensing electrode signal, which shows an electrical disturbance in fluid potential that also affected the original signal. In this example, the signal may be averaged over all wells in a thumbnail region (100 by 100 wells) and the scale factor α is 2.3.

In various embodiments, a signal corrected as discussed herein may then be further corrected for additional potential sources of errors or noise (e.g., background fitting or subtraction and/or phase effects). For example, a signal corrected as discussed herein may be further processed, modified, and/or corrected using the teachings of Davey et al., "Predictive Model for Use in Sequencing-by-Synthesis," U.S. Pat. No. 8,666,678, issued Mar. 4, 2014; Rearick et al., "Models for Analyzing Data from Sequencing-by-Synthesis Operations," U.S. Pat. Appl. Publ. No. 2012/0172241, published Jul. 5, 2012; and Hubbell, "Time-Warped Background Signal for Sequencing-by-Synthesis Operations," U.S. Pat. Appl. Publ. No. 2012/0173158, published Jul. 5, 2012, which are all incorporated by reference herein in their entirety.

Figure 9A:
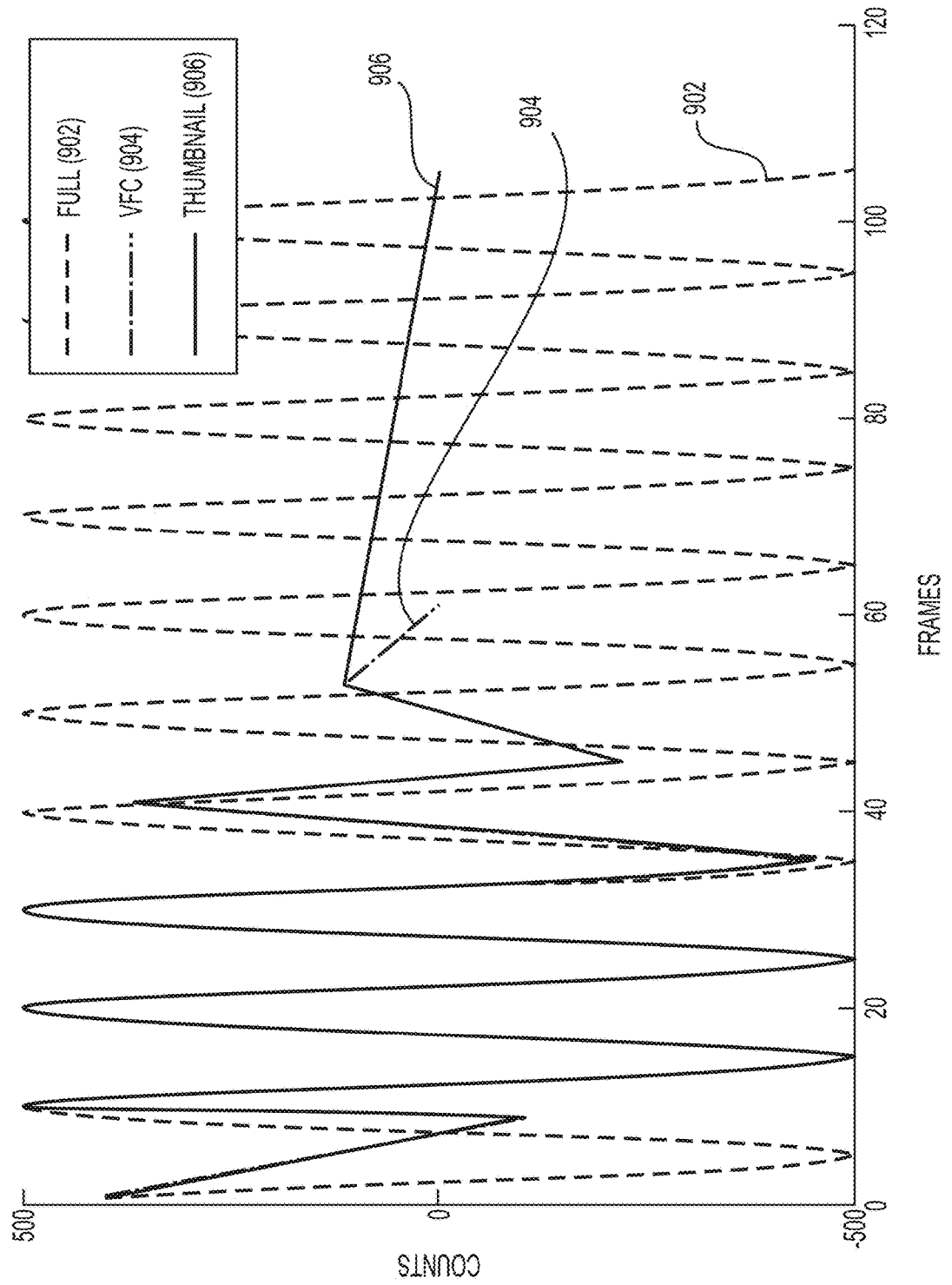
FIG. 9A illustrates an example of simulated injection of noise in sensing electrode signal, according to exemplary embodiments of the present disclosure.

FIG. 9A illustrates an example of simulated injection of noise in a sensing electrode signal. In this example, the noise may be numerically-injected, common-mode noise at a particular flow. The x-axis represents time during sensing, expressed in frames. The y-axis represents voltage, expressed in counts. Curve 902 (see sinusoidal curve) depicts a curve representing the full noise time series without any variable frame compression. Curve 904 (see curve terminating shortly after 60 frames) depicts a curve representing the waveform after variable frame compression. Curve 906 (see curve with slope terminating at about 0 counts) depicts a curve representing the waveform that would appear in thumbnail data having undergone a series of interpolation and extrapolation attempting to transform variable frame compression data to full data. Such sensing electrode signals including simulated injection of noise may be used to evaluate the effect of noise and the efficacy of signal correction.

Figure 9B:
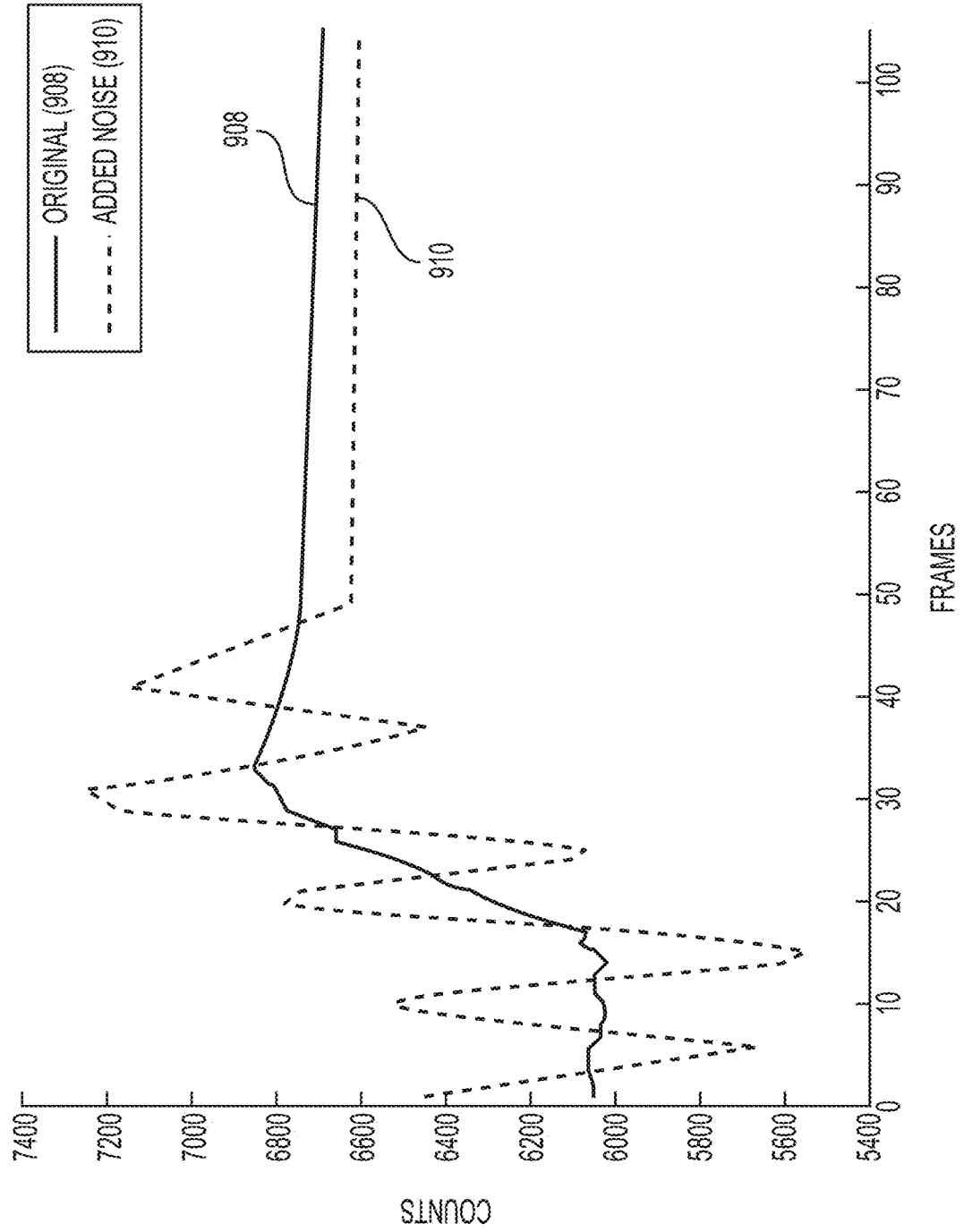
FIG. 9B illustrates an example of simulated injection of noise in well signal, according to exemplary embodiments of the present disclosure.

FIG. 9B illustrates an example of simulated injection of noise in a well signal. In this example, the noise may be numerically-injected, common-mode noise at a particular flow. The x-axis represents time during sensing, expressed in frames. The y-axis represents voltage, expressed in counts. Curve 908 (see relatively smooth curve) represents an original waveform. Curve 910 (see curve with multiple peaks) represents the original waveform to which noise has been added. Such well signals including simulated injection of noise may be used to evaluate the effect of noise and the efficacy of signal correction.

Figures 10A, 10B:
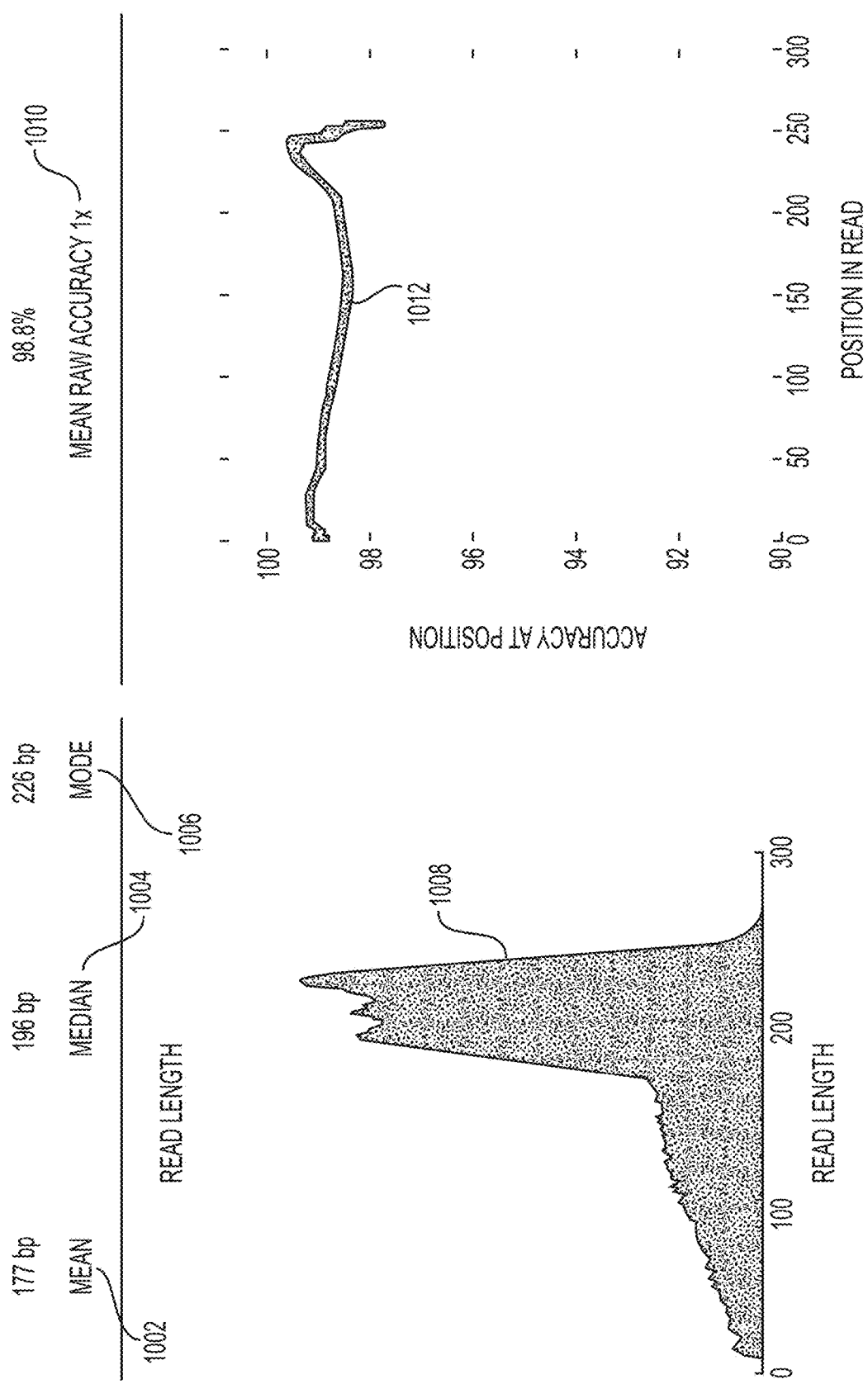
FIGS. 10A and 10B illustrate examples of run statistics for a run including a relatively small amount of simulated noise, according to exemplary embodiments of the present disclosure.

FIGS. 10A and 10B illustrate examples of run statistics for a run including a relatively small amount of simulated noise. The run statistics, as shown in FIG. 10A, may include mean read length 1002, median read length 1004, and mode read length 1006, along with a histogram 1008 of read lengths. The run statistics, as shown in FIG. 10B, may include mean raw accuracy 1010, and a plot 1012 of accuracy as a function of position in the read. In this example, the noise may be a 200-count peak-to-peak noise. As may be seen in FIGS. 10A and 10B, the relatively small amount of simulated noise may have a minimal effect on the run.

Figures 11A, 11B:
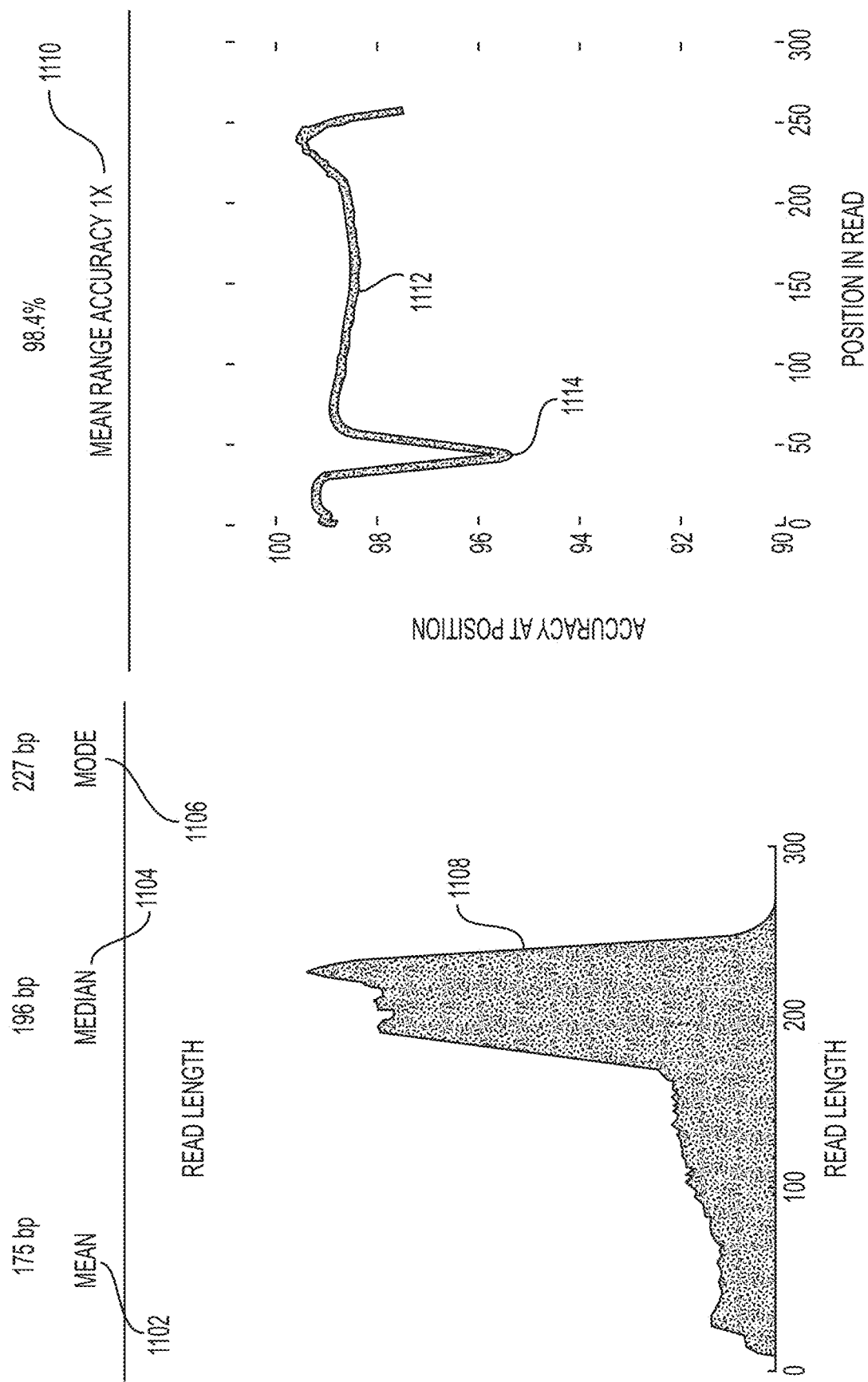
FIGS. 11A and 11B illustrate examples of run statistics for a run including a relatively large amount of simulated noise, according to exemplary embodiments of the present disclosure.

FIGS. 11A and 11B illustrate examples of run statistics for a run including a relatively large amount of simulated noise. The run statistics, as shown in FIG. 11A, may include mean read length 1102, median read length 1104, and mode read length 1106, along with a histogram 1108 of read lengths. The run statistics, as shown in FIG. 11B, may include mean raw accuracy 1110, and a plot 1112 of accuracy as a function of position in the read. In this example, the noise may be a 1,000-count peak-to-peak noise. As can be seen in FIGS. 11A and 11B, the relatively large amount of simulated noise may have a severe effect on the run, including a severe drop 1114 in accuracy around position 50 and a lower mean raw accuracy of 98.4% (see FIG. 11B, compared with 98.8% in FIG. 10B).

Figure 12B:
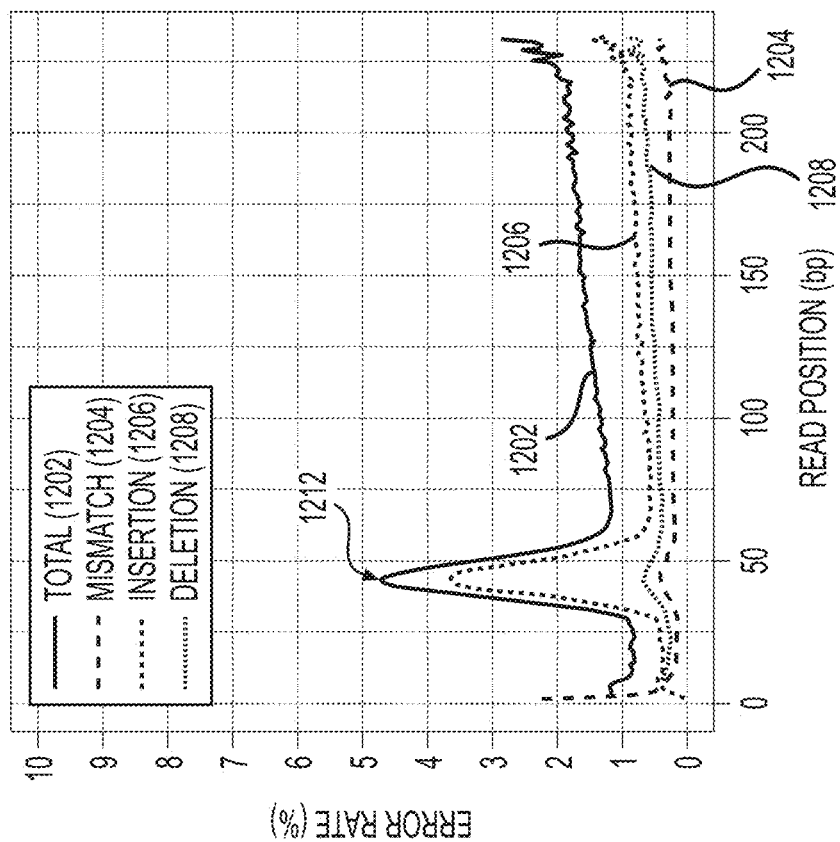
FIGS. 12A and 12B illustrate run statistics and plots of error rates as a function of read position without correction for runs including a relatively large amount of simulated noise such as in FIGS. 11A and 11B, according to exemplary embodiments of the present disclosure.
Figure 12A:
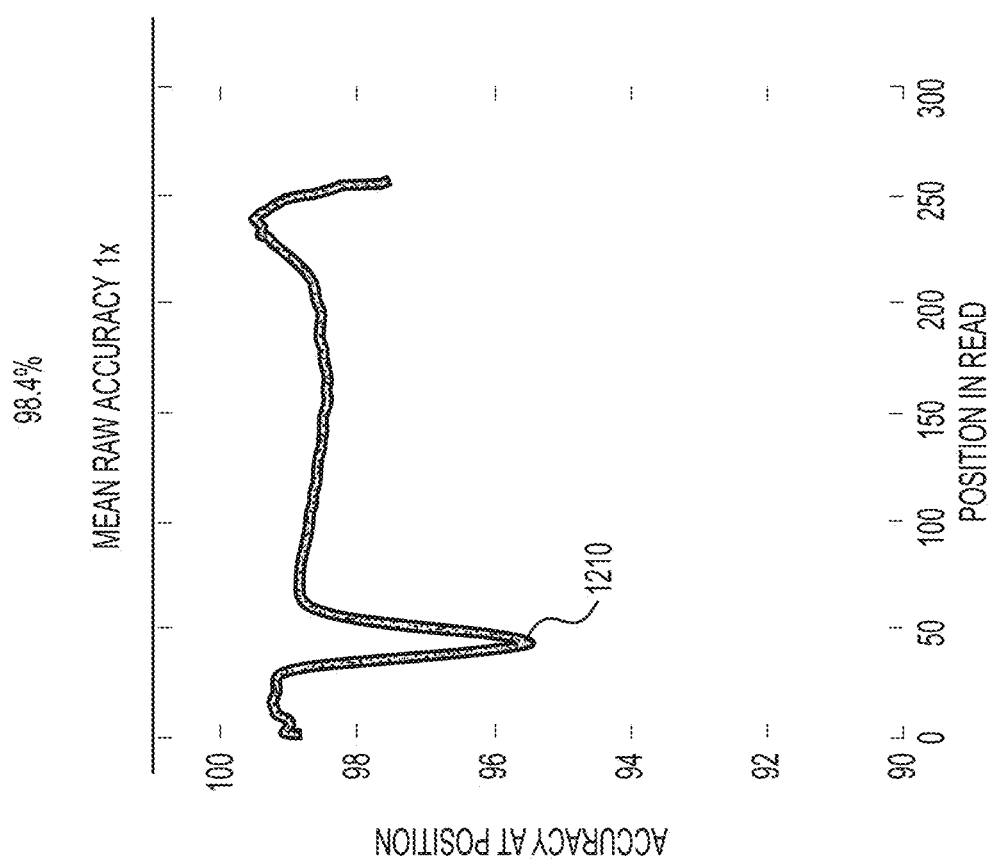

FIGS. 12A and 12B illustrate run statistics and plots of error rates as a function of read position without correction for runs including a relatively large amount of simulated noise such as in FIGS. 11A and 11B. FIG. 12B shows total error rates (in curve 1202, see top curve), insertion error rates (in curve 1206, see second curve from the top), deletion error rates (in curve 1208, see third curve from the top), and mismatch error rates (in curve 1204, see bottom curve). Without the correction, there may be a severe drop 1210 in accuracy (see FIG. 12A) and increase in error rates 1212 (see FIG. 12B) around position 50.

Figure 13B:
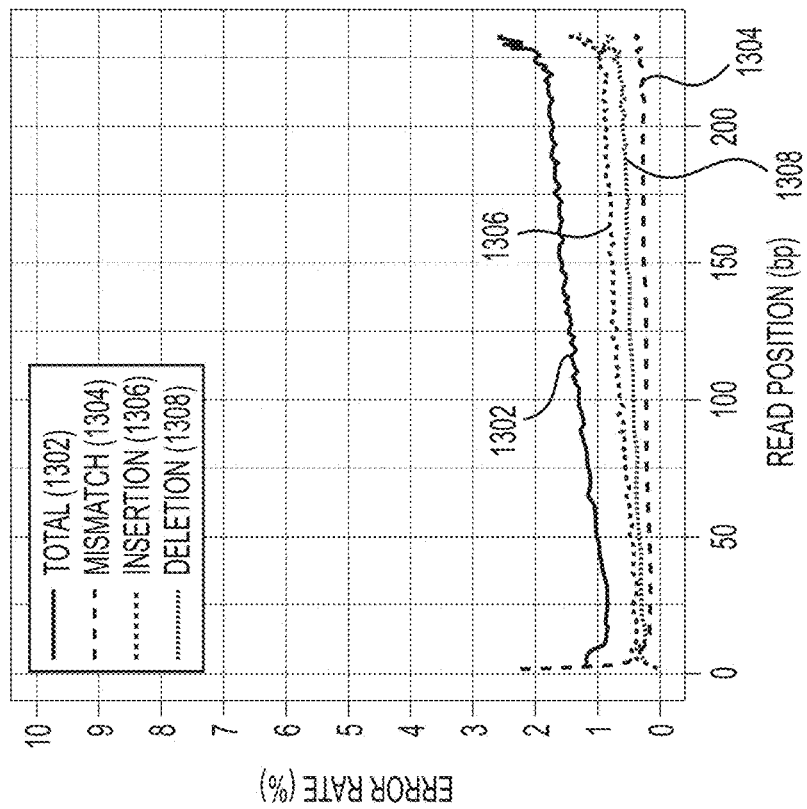
FIGS. 13A and 13B illustrate run statistics and plots of error rates as a function of read position with correction for runs including a relatively large amount of simulated noise such as in FIGS. 11A and 11B, according to exemplary embodiments of the present disclosure.
Figure 13A:

FIGS. 13A and 13B illustrate run statistics and plots of error rates as a function of read position with correction for runs including a relatively large amount of simulated noise such as in FIGS. 11A and 11B. FIG. 13B shows total error rates (in curve 1302, see top curve), insertion error rates (in curve 1306, see second curve from the top), deletion error rates (in curve 1308, see third curve from the top), and mismatch error rates (in curve 1304, see bottom curve). With the correction as described herein with a scale factor $\alpha$ of 2.0 inferred by algorithm matching the inserted noise magnitude, there may be no longer a severe drop in accuracy (see FIG. 13A, compared with FIG. 12A) and increase in error rates (see FIG. 13B, compared with FIG. 12B) around position 50.

According to various exemplary embodiments, there may be provided a method for correcting nucleotide incorporation signals for fluid potential effects or disturbances arising in nucleic acid sequencing-by-synthesis, comprising: (a) disposing a plurality of template polynucleotide strands in a plurality of defined spaces disposed on a sensor array, at least some of the template polynucleotide strands having a sequencing primer and a polymerase bound therewith; (b) exposing the template polynucleotide strands with the sequencing primer and a polymerase bound therewith to a series of flows of nucleotide species flowed according to a predetermined ordering through a fluid manifold, the fluid manifold comprising passages for flowing nucleotide species and a branch passage for flowing a solution not comprising nucleotide species, the branch passage comprising a reference electrode and a sensing electrode; (c) obtaining a plurality of nucleotide incorporation signals corresponding to the plurality of defined spaces, the nucleotide incorporation signals having a signal intensity related to a number of nucleotide incorporations having occurred in the corresponding defined space; and (d) correcting at least some of the plurality of nucleotide incorporation signals for fluid potential effects or disturbances using a mathematical transformation comprising a scale factor determined based on signals obtained from the sensing electrode for each of a plurality of regions of defined spaces on the sensor array.

In such a method, correcting the at least some of the plurality of nucleotide incorporation signals may comprise using an expression $w_c(t)=w(t)-\alpha\, s(t)$, where $w_c(t)$ represents a corrected sensor signal, $w(t)$ represents an uncorrected sensor signal, $s(t)$ represents a sensing electrode signal, and $\alpha$ represents the scale factor. Determining the scale factor may comprise selecting a fixed $\alpha$ as starting point. Determining the scale factor may further comprise calculating $w_c(t)$ for each of a plurality of regions of defined spaces on the sensor array. Determining the scale factor may further comprise calculating an average trace $\overline{w_c}(t)$ for the $w_c(t)$ calculated for each of a plurality of regions of defined spaces on the sensor array to remove non-common-mode noise. Determining the scale factor may further comprise fitting $\overline{w_c}(t)$ with local polynomials. The local polynomials may be determined using a digital filter, such as a Savitzky-Golay filter, and may be determined using a second order Savitzky-Golay filter. Determining the scale factor may further comprise calculating a mean square error of $\overline{w_c}(t)$ from the fitting. Determining the scale factor may further comprise selecting the optimal scale factor $\alpha$ that minimizes the mean square error.

According to various exemplary embodiments, there may be provided a non-transitory machine-readable storage medium comprising instructions which, when executed and/or implemented by a processor, cause the processor to perform a method for correcting nucleotide incorporation signals for fluid potential effects or disturbances arising in nucleic acid sequencing-by-synthesis comprising (a) exposing a plurality of template polynucleotide strands disposed in a plurality of defined spaces disposed on a sensor array and having a sequencing primer and a polymerase bound therewith to a series of flows of nucleotide species flowed according to a predetermined ordering through a fluid manifold, the fluid manifold comprising passages for flowing nucleotide species and a branch passage for flowing a solution not comprising nucleotide species, the branch passage comprising a reference electrode and a sensing electrode; (b) obtaining a plurality of nucleotide incorporation signals corresponding to the plurality of defined spaces, the nucleotide incorporation signals having a signal intensity related to a number of nucleotide incorporations having occurred in the corresponding defined space; and (c) correcting at least some of the plurality of nucleotide incorporation signals for fluid potential effects or disturbances using a mathematical transformation comprising a scale factor determined based on signals obtained from the sensing electrode for each of a plurality of regions of defined spaces on the sensor array.

In such a non-transitory machine-readable storage medium, correcting the at least some of the plurality of nucleotide incorporation signals may comprise using an expression $w_c(t)=w(t)-\alpha\, s(t)$, where $w_c(t)$ represents a corrected sensor signal, $w(t)$ represents an uncorrected sensor signal, $s(t)$ represents a sensing electrode signal, and $\alpha$ represents the scale factor. Determining the scale factor may comprise selecting a fixed $\alpha$ as starting point. Determining the scale factor may further comprise calculating $w_c(t)$ for each of a plurality of regions of defined spaces on the sensor array. Determining the scale factor may further comprise calculating an average trace $\overline{w_c}(t)$ for the $w_c(t)$ calculated for each of a plurality of regions of defined spaces on the sensor array to remove non-common-mode noise. Determining the scale factor may further comprise fitting $\overline{w_c}(t)$ with local polynomials. The local polynomials may be determined using a digital filter, such as a Savitzky-Golay filter, and may be determined using a second order Savitzky-Golay filter. Determining the scale factor may further comprises calculating a mean square error of $\overline{w_c}(t)$ from the fitting. Determining the scale factor may further comprises selecting the optimal scale factor $\alpha$ that minimizes the mean square error.

In various embodiments, general sequencing-by-synthesis aspects relating to the present disclosure may comprise one or more features described in Rothberg et al., U.S. Pat. No. 7,948,015, and Rothberg et al., U.S. Pat. Appl. Publ. Nos. 2010/0137143, 2009/0026082, and 2010/0282617, which are all incorporated by reference herein in their entirety.

In various embodiments, nucleic acid sequencing data compression aspects relating to the present disclosure may comprise one or more features described in Sugnet et al., U.S. Pat. Appl. Publ. No. 2013/0231870, published Sep. 5, 2013, which is incorporated by reference herein in their entirety.

In various embodiments, base calling aspects relating to the present disclosure may include performing or implementing one or more of the teachings disclosed in Davey et al., U.S. Pat. No. 8,666,678, issued Mar. 4, 2014, which is incorporated by reference herein in its entirety. Other aspects of signal processing and base calling may include performing or implementing one or more of the teachings disclosed in Davey et al., U.S. Pat. Appl. Publ. No. 2012/0173159, published Jul. 5, 2012, and Sikora et al., U.S. Pat. Appl. Publ. No. 2013/0060482, published Mar. 7, 2013, which are all incorporated by reference herein in their entirety.

In various embodiments, flow ordering aspects relating to the present disclosure may comprise one or more features described in Hubbell et al., U.S. Pat. Appl. Publ. No. 2012/0264621, published Oct. 18, 2012, which is incorporated by reference herein in its entirety.

Figures 14A, 14B:
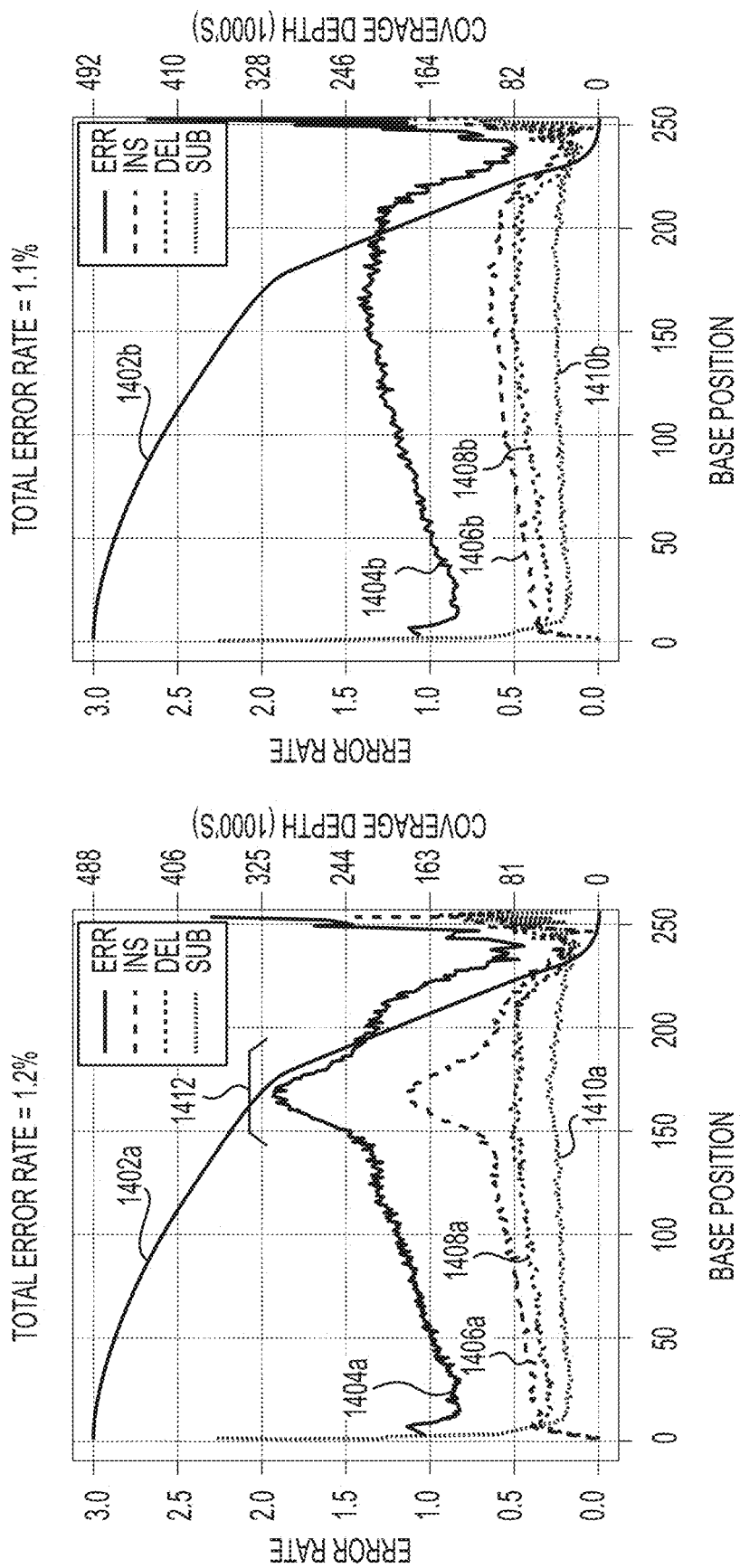
FIGS. 14A and 14B illustrate error rates and coverage depth for runs without (FIG. 14A) and with (FIG. 14B) fluid potential artifact correction, according to exemplary embodiments of the present disclosure.

FIGS. 14A and 14B illustrate error rates and coverage depth for runs without (FIG. 14A) and with (FIG. 14B) fluid potential artifact correction. FIG. 14A shows data for a user-compromised run affected by an elevated error rate due to a user touching tubings. FIG. 14B shows the same, after correction for fluid potential artifact. The x-axis represents the base position. The y-axis represents the error rate (on the left) and coverage depth (on the right). Shown are coverage depth curves $1402a$ and $1402b$ (see curves starting in the upper left corner of the plots). Also shown are total error rates (in curves $1404a$ and $1404b$, see top curves), insertion error rates (in curves $1406a$ and $1406b$, see second curves from the top), deletion error rates (in curves $1408a$ and $1408b$, see third curves from the top), and substitution error rates (in curves $1410a$ and $1410b$, see bottom curves). Without the correction, there is a significant increase in error rate (see region $1412$ of FIG. 14A between positions 150 and 200 and compare with FIG. 14B). Also, the total error rate was 1.2% with 66.3 million high-quality (Q20) bases in FIG. 14A compared to 1.1% with 68 million high-quality (Q20) bases in FIG. 14B.

In various embodiments, fluid potential artifact correction methods, systems, and non-transitory machine-readable storage media may reduce a total error rate in a user-compromised run by about 0.1% (in absolute percentage value), which represents a relative reduction in total error rate expressed in absolute percentage value of about $(|1.1\%-1.2\%|)/1.2\%=0.08333333$ or about 8.3%. In addition, fluid potential artifact correction methods, systems, and non-transitory machine-readable storage media may increase a number of high-quality (Q20) bases in a user-compromised run by about 1.7 million (in absolute number of bases), which represents a relative augmentation in high-quality (Q20) bases of about $(|68-66.3|)/66.3=0.0256410$ or about 2.6%. It should be noted, however, that error rate and number of high-quality (Q20) bases depend on numerous factors and experiment conditions, which may otherwise affect accuracy and in some cases may be more significant than fluid potential artifacts.

According to various embodiments, some errors related to disturbances in fluid potential may be corrected using a sensing electrode and mathematical transformation as described herein. It should be noted, however, that this correction approach may not correct all sources of error. In some embodiments, various fluid potential correction embodiments as described herein may be combined with other signal correction algorithms addressing other sources of error (e.g., background effects or other distortion effects).

Figure 15A:
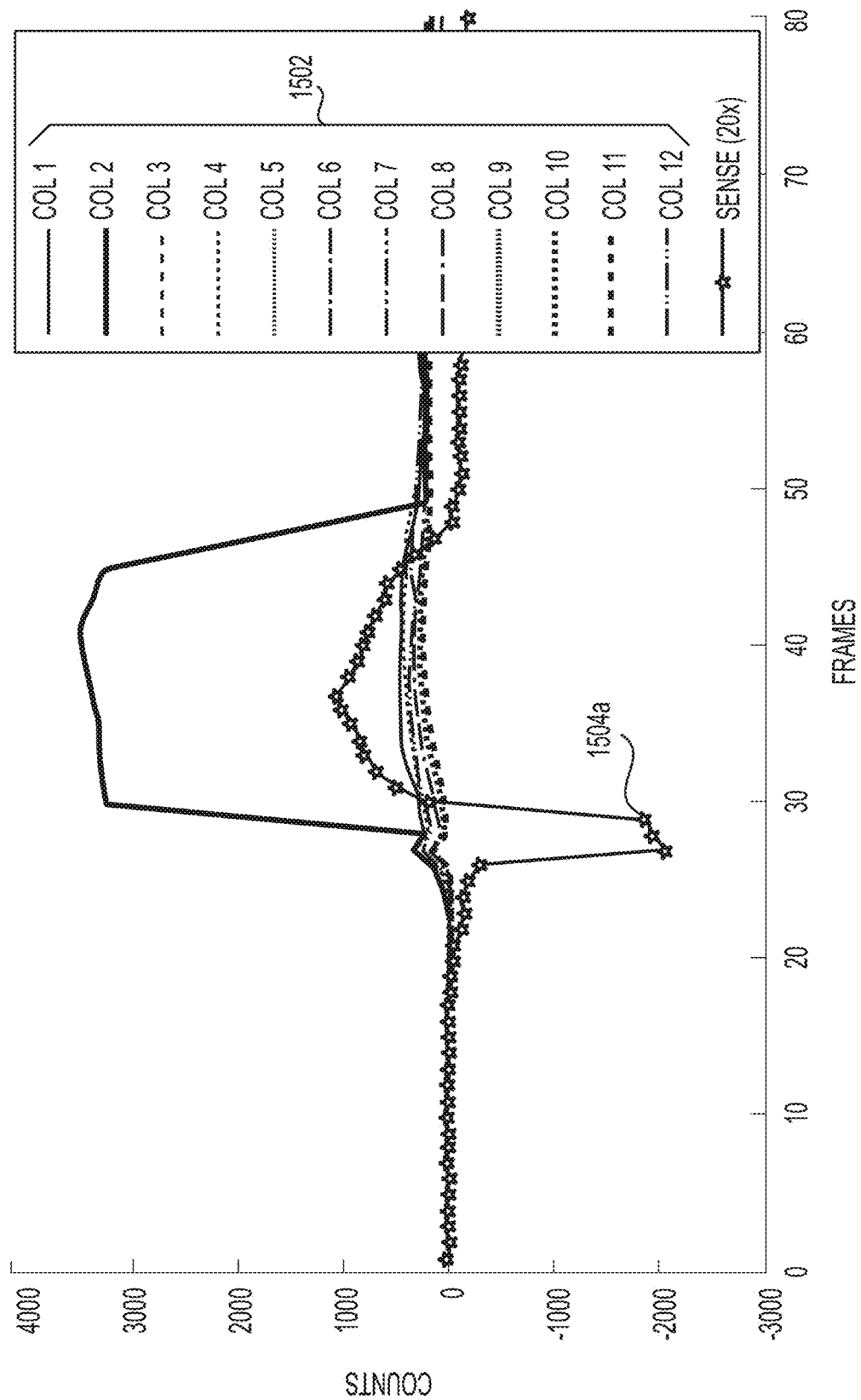
FIGS. 15A and 15B illustrate examples of simultaneous measurements showing different response across columns for a non-common mode noise, according to exemplary embodiments of the present disclosure.
Figure 15B:
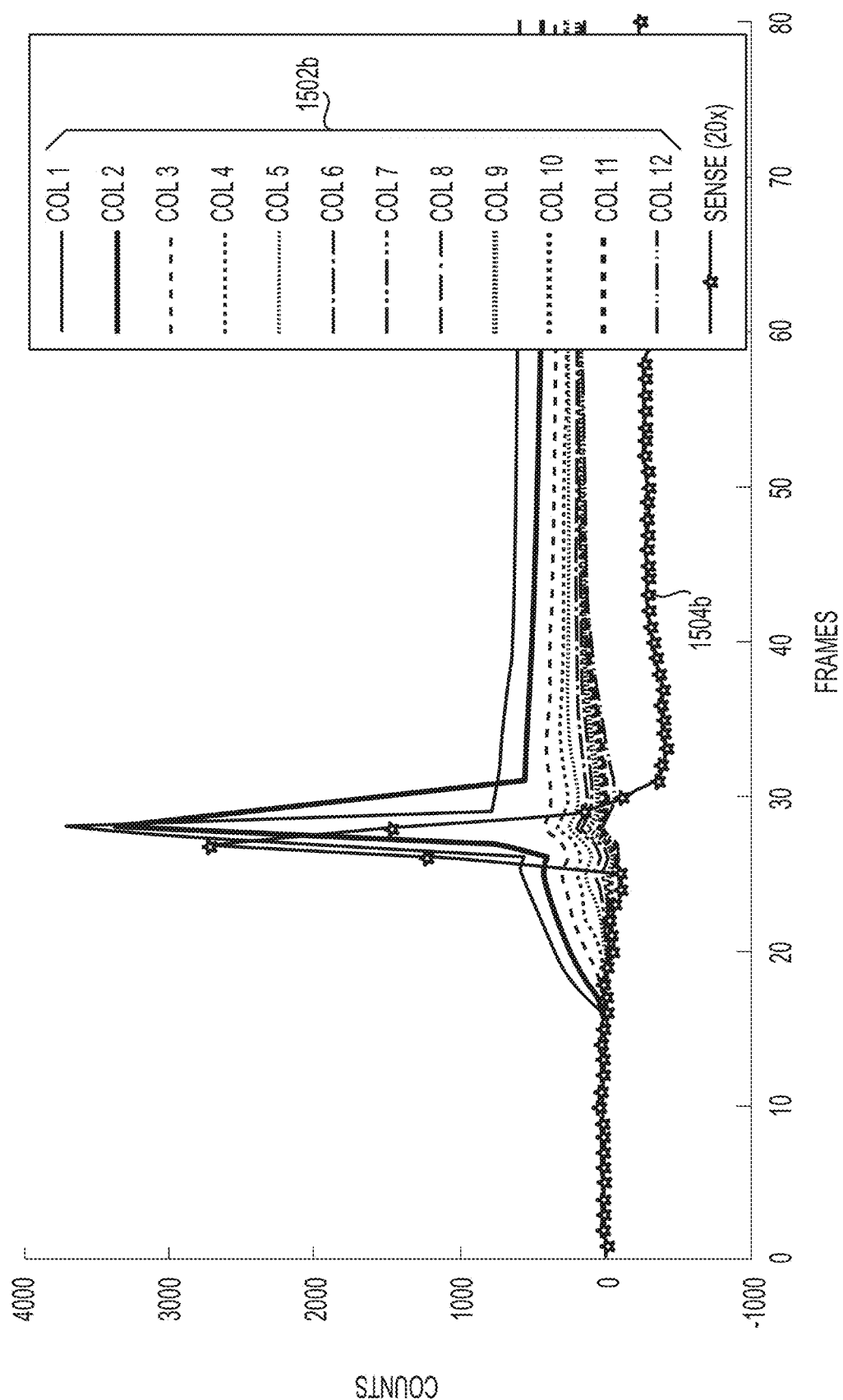

FIGS. 15A and 15B illustrate examples of simultaneous measurements showing different response across columns for a non-common mode noise. The x-axis represents time during sensing, expressed in frames. The y-axis represents voltage, expressed in counts. Shown in each of FIGS. 15A and 15B are average live traces for a thumbnail row region (e.g., 100 by 100 wells) for 12 columns (see curves of column portions $1502a$ and $1502b$) and the sensor electrode (see curves $1504a$ and $1504b$). The noise here may be due to electrical noise induced by bubbles blocking some wells. Traces differ significantly depending on the row region (and across columns one can note some outlier traces for a given row region).

Figure 16A:
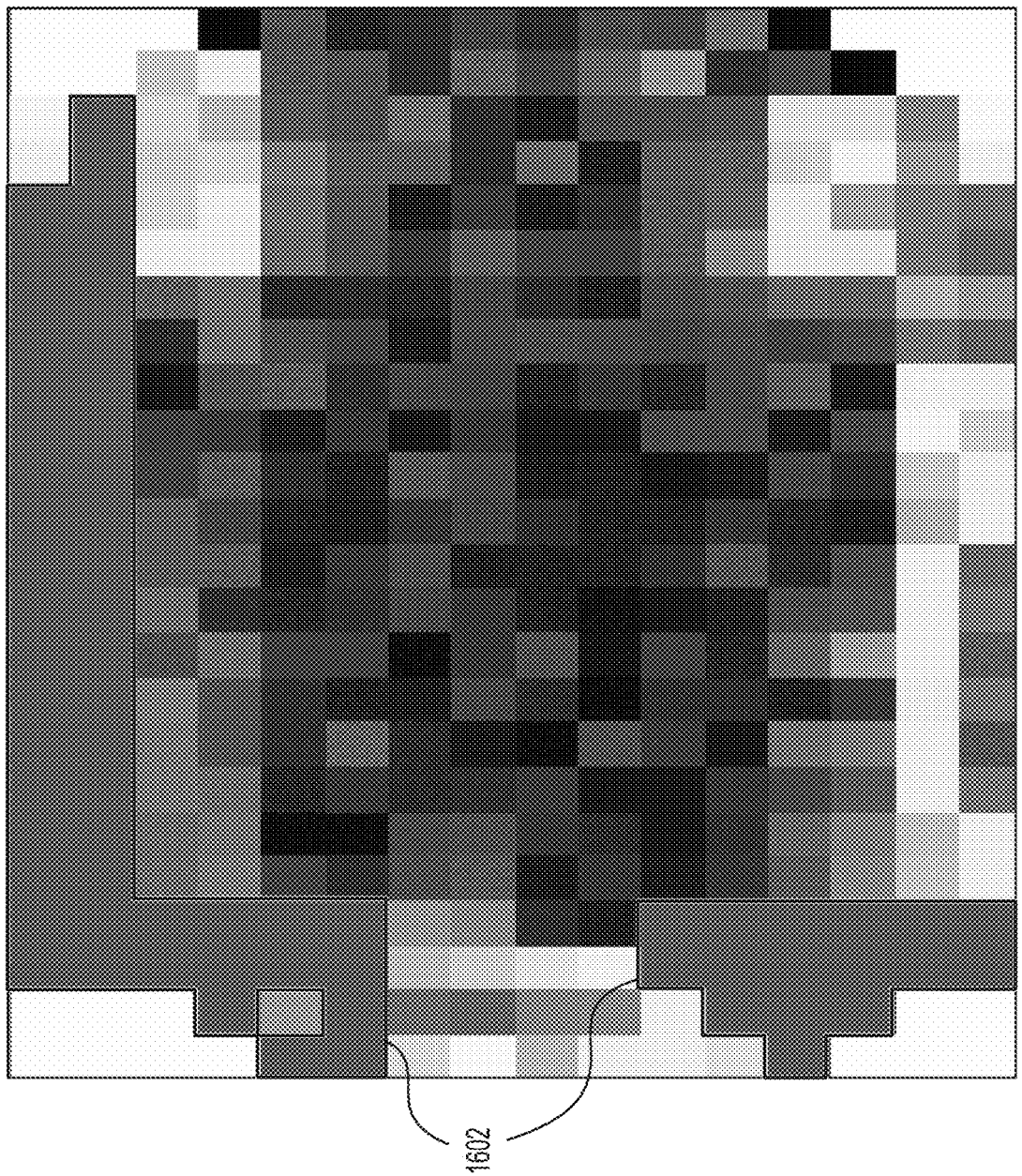
FIGS. 16A and 16B illustrate examples of a spatial distribution of error rates for a non-common mode noise after a flow resulting in significant errors, according to exemplary embodiments of the present disclosure.
Figure 16B:
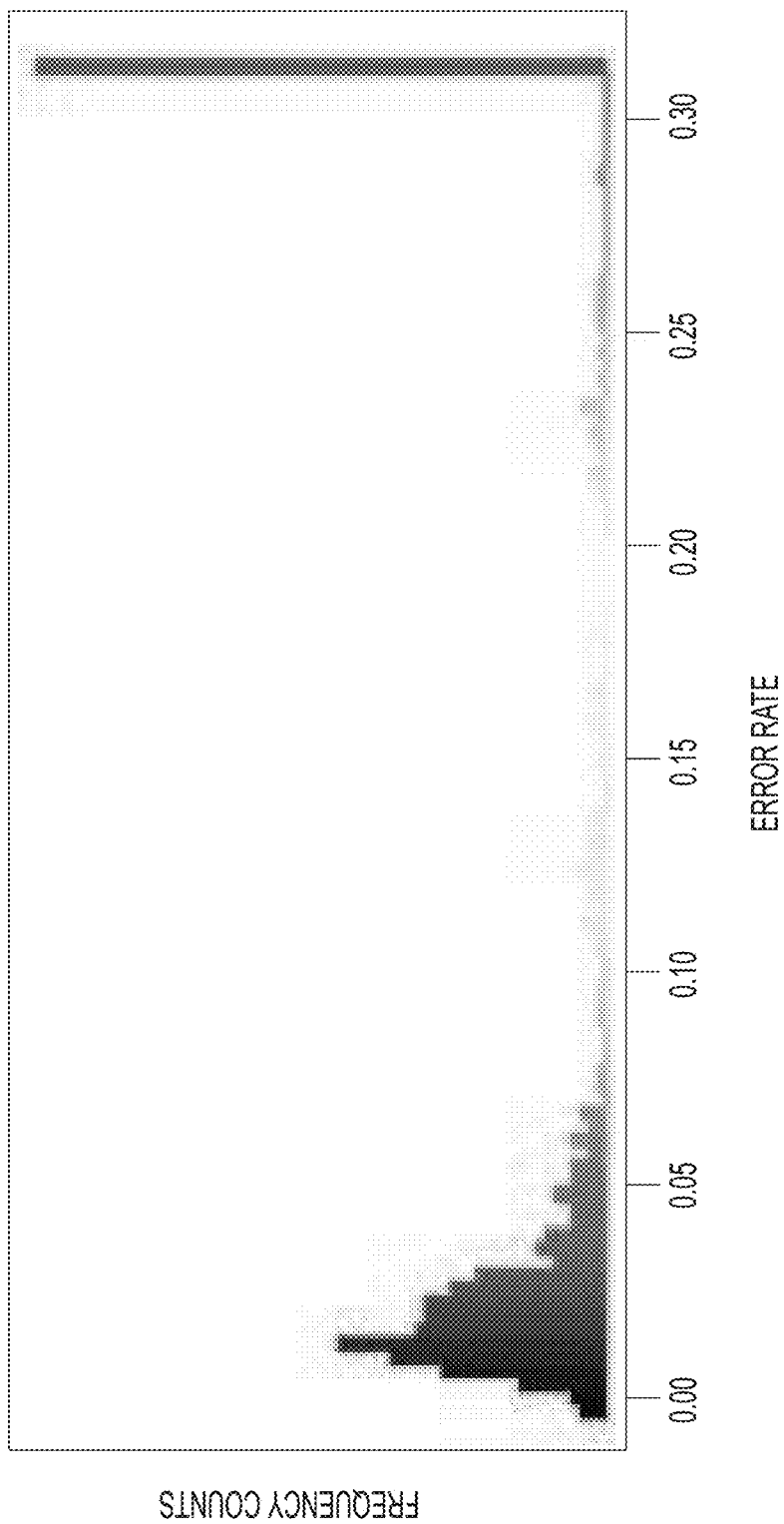

FIGS. 16A and 16B illustrate examples of a spatial distribution of error rates for a non-common mode noise after a flow resulting in significant errors. The x-axis and y-axis of FIG. 16A represent length along two sides of a sensor, with each block corresponding to a region of sensors on a chip. As shown in FIG. 16A, the blocks have a heterogeneous shading throughout many of the regions of the sensors on the chip. As can be seen, errors (see regions $1602$ of FIG. 16A) appear the blocks in adjacent regions that have a homogenous shading. These error also may be mostly associated with a small number of regions, which tend to be along the periphery of the array of regions. Further analysis may have shown that these regions have non-common mode noise that cannot be removed using a sensing electrode and correction method as described herein. FIG. 16B illustrates an example of the spatial distribution of error rates of FIG. 16A in a bar graph, where the x-axis of FIG. 16B represents the error rate and the y-axis of FIG. 16B represents the frequency counts.

Figure 17A:
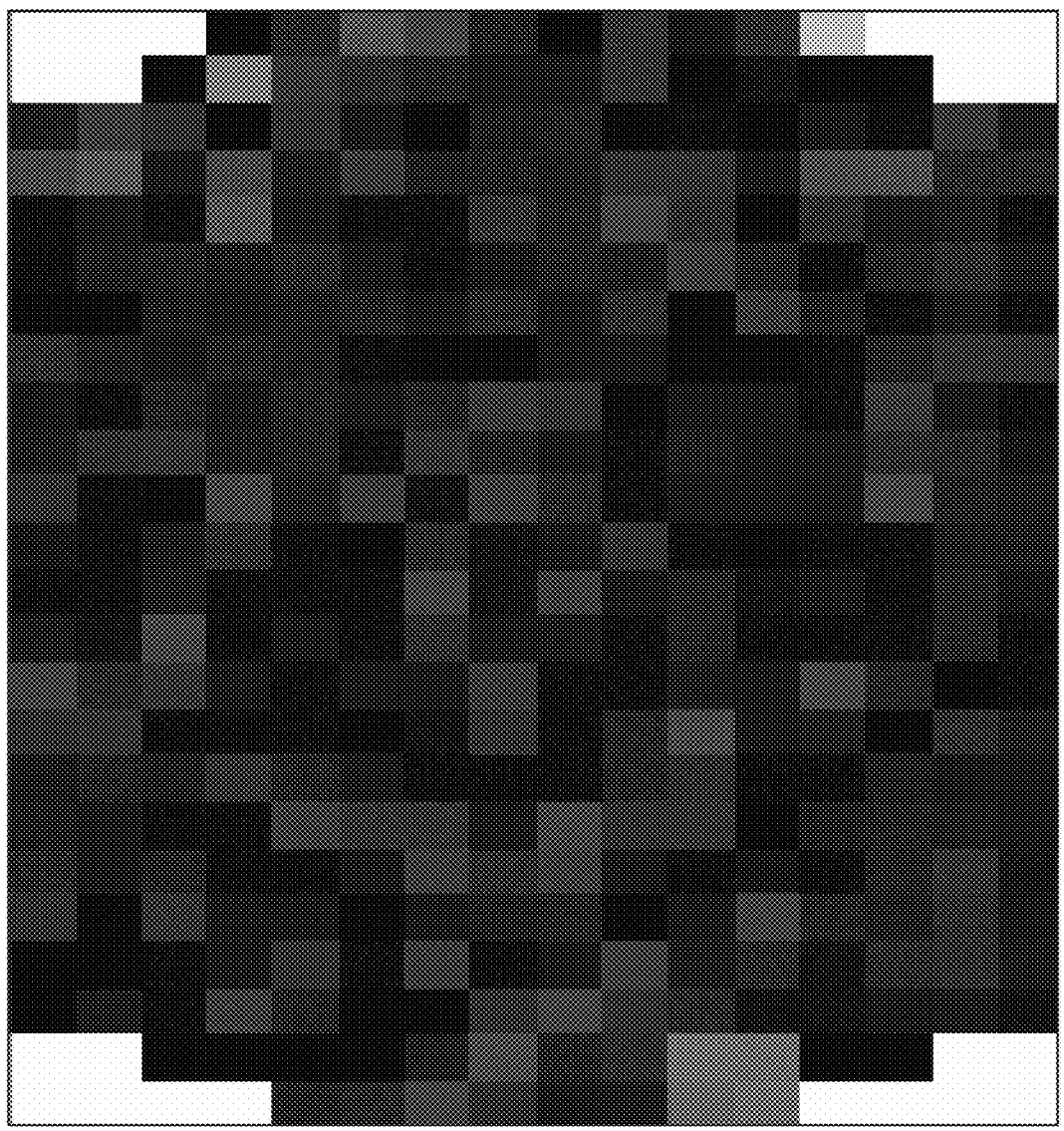
FIGS. 17A and 17B illustrate examples of a spatial distribution of error rates for a non-common mode noise after a flow not resulting in significant errors, according to exemplary embodiments of the present disclosure.
Figure 17B:
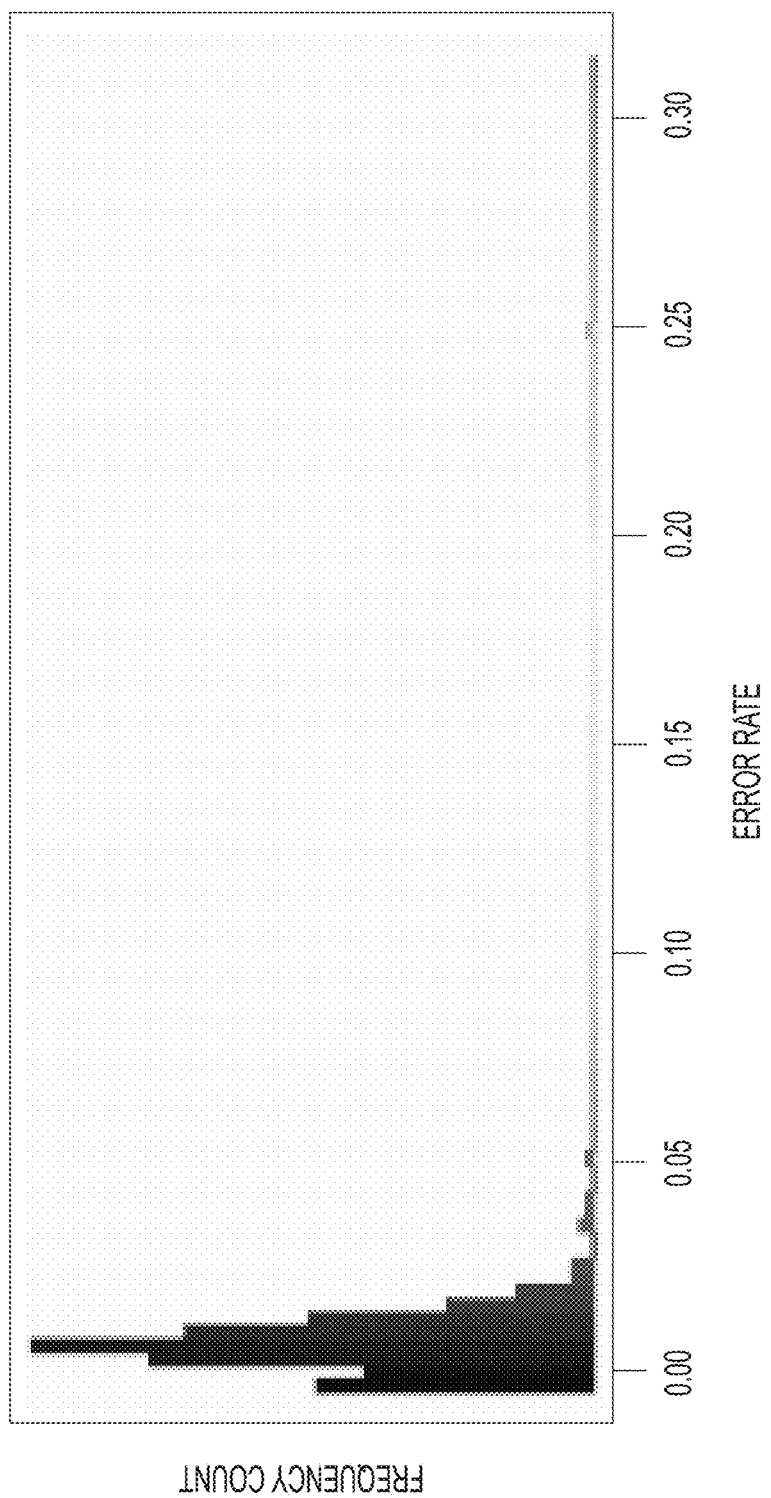

FIGS. 17A and 17B illustrate examples of a spatial distribution of error rates for a non-common mode noise after a flow not resulting in significant errors. The x-axis and y-axis of FIG. 17A represent length along two sides of a sensor, with each block corresponding to a region of sensors on a chip. As shown in FIG. 17A, the blocks have a heterogeneous shading throughout the regions of the sensors on the chip. FIG. 17B illustrates an example of the spatial distribution of error rates of FIG. 17A in a bar graph, where the x-axis of FIG. 17B represents the error rate and the y-axis of FIG. 17B represents the frequency counts. As can be seen by comparing the FIG. 16A to FIG. 17A and FIG. 16B to FIG. 17B, the errors shown in FIGS. 17A and 17B were relatively rare in this case, allowing a baseline comparison with FIGS. 16A and 16B.

Figure 18:
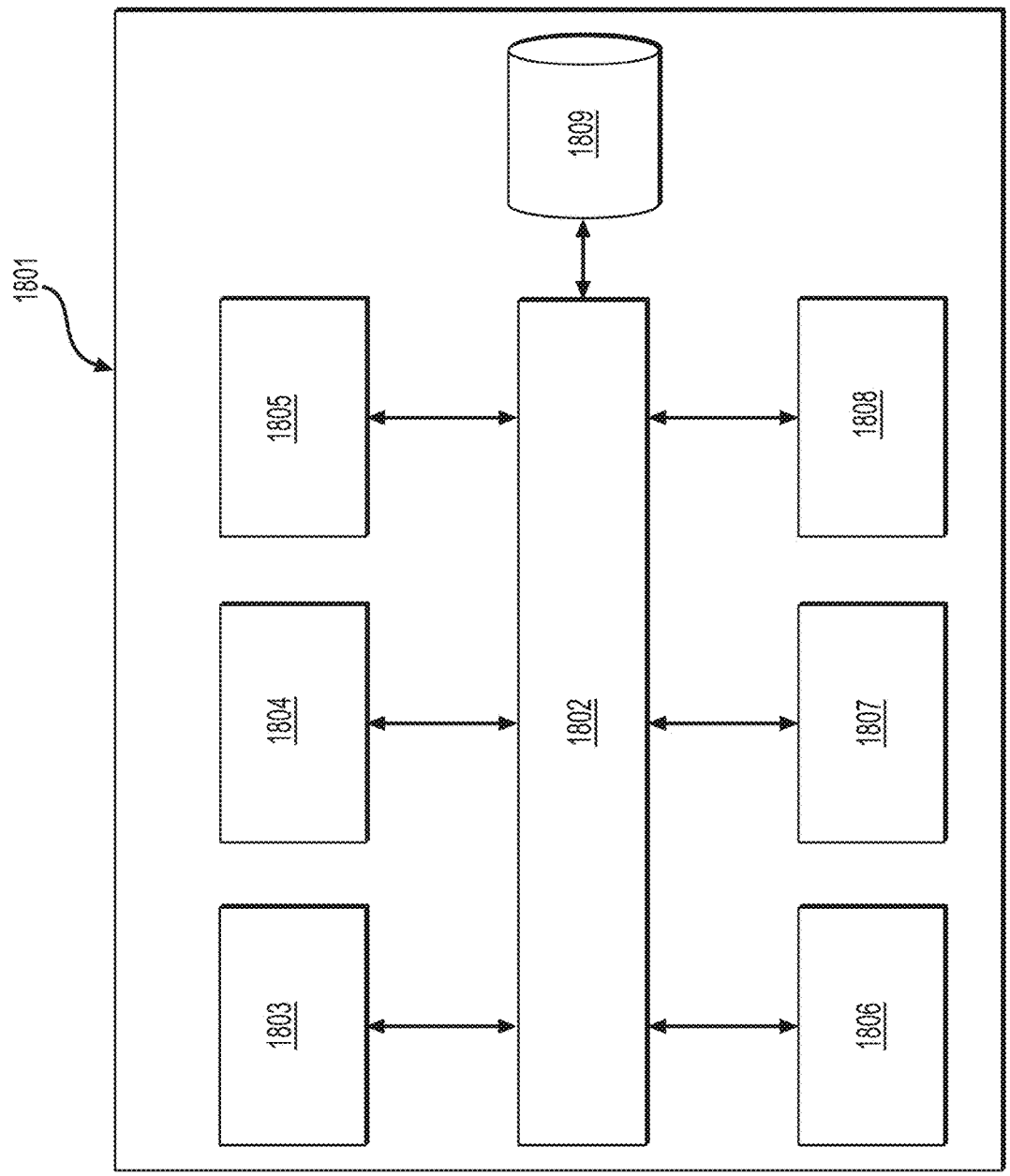
FIG. 18 illustrates an exemplary computer system, according to exemplary embodiments of the present disclosure.

FIG. 18 illustrates an exemplary computer system. The computer system $1801$ may include a bus $1802$ or other communication mechanism for communicating information, a processor $1803$ coupled to the bus $1802$ for processing information, and a memory $1805$ coupled to the bus $1802$ for dynamically and/or statically storing information. The computer system $1801$ can also include one or more co-processors $1804$ coupled to the bus $1802$, such as GPUs and/or FPGAs, for performing specialized processing tasks; a display $1806$ coupled to the bus $1802$, such as a cathode ray tube ("CRT") and/or liquid crystal display ("LCD"), for displaying information to a computer user; an input device $1807$ coupled to the bus $1802$, such as a keyboard including alphanumeric and other keys, for communicating information and command selections to the processor $1803$; a cursor control device $1808$ coupled to the bus $1802$, such as a mouse, a trackball, and/or cursor direction keys for communicating direction information and command selections to the processor $1803$ and for controlling cursor movement on display $1806$; and one or more storage devices $1809$ coupled to the bus $1802$, such as a solid state drive, a hard disk drive, a magnetic disk, and/or an optical disk, for storing information and instructions. The memory $1805$ may include a random access memory ("RAM") or other dynamic storage device and/or a read only memory ("ROM") or other static storage device. Such an exemplary computer system with suitable software may be used to perform the embodiments described herein. More generally, in various embodiments, one or more features of the teachings and/or embodiments described herein may be performed or implemented using appropriately configured and/or programmed hardware and/or software elements.

Examples of hardware elements may include processors, microprocessors, input(s) and/or output(s) ("I/O") device(s) (or peripherals) that are communicatively coupled via a local interface circuit, circuit elements (e.g., transistors, resistors, capacitors, inductors, and so forth), integrated circuits, application specific integrated circuits ("ASIC"), programmable logic devices ("PLD"), digital signal processors ("DSP"), field programmable gate array ("FPGA"), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory. The processor can be any custom made or commercially available processor, a central processing unit ("CPU"), an auxiliary processor among several processors associated with the computer, a semiconductor based microprocessor (e.g., in the form of a microchip or chip set), a macroprocessor, or generally any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem; for accessing another device, system, or network), a radio frequency ("RF") or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces ("API"), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system ("O/S"), which may control the execution of other computer programs such as the system, and provides scheduling, input-output control, file and data management, memory management, communication control, etc.

According to various embodiments, one or more features of teachings and/or embodiments described herein may be performed or implemented using an appropriately configured and/or programmed non-transitory machine-readable medium or article that may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc ("CD-ROM"), recordable compact disc ("CD-R"), rewriteable compact disc ("CD-RW"), optical disk, magnetic media, magneto-optical media, removable memory cards or disks, various types of Digital Versatile Disc ("DVD"), a tape, a cassette, etc., including any medium suitable for use in a computer. Memory can include any one or a combination of volatile memory elements (e.g., random access memory ("RAM", such as DRAM, SRAM, SDRAM, etc.)) and nonvolatile memory elements (e.g., ROM, EPROM, EEROM, Flash memory, hard drive, tape, CD-ROM, etc.). Moreover, memory can incorporate electronic, magnetic, optical, and/or other types of storage media. Memory can have a distributed, clustered, remote, or cloud architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

Unless otherwise specifically designated herein, terms, techniques, and symbols of biochemistry, cell biology, genetics, molecular biology, nucleic acid chemistry, nucleic acid sequencing, and organic chemistry used herein follow those of standard treatises and texts in the relevant field.

Although the present description described in detail certain embodiments, other embodiments are also possible and within the scope of the present invention. For example, those skilled in the art may appreciate from the present description that the present teachings may be implemented in a variety of forms, and that the various embodiments may be implemented alone or in combination. Variations and modifications will be apparent to those skilled in the art from consideration of the specification and figures and practice of the teachings described in the specification and figures, and the claims.

What is claimed is:

1. A method for measuring a reaction product, the method comprising:

flowing a reagent solution into a flow cell in fluid communication with an array of electronic sensors cooperatively engaged with the flow cell, wherein a first subset of the array of electronic sensors is exposed to the reagent solution within the flow cell, a second subset of the array of electronic sensors is free of contact with the reagent solution within the flow cell, and wherein the reagent solution reacts to provide a reaction product;

measuring a first response of the first subset of the array of electronic sensors to the reaction product;

measuring a second response of the second subset of the array of electronic sensors, the second subset of the array of electronic sensors in electrical communication with a sensor electrode in fluid communication with the flow cell; and adjusting the first response of the first subset of the array of electronic sensors based on the second response of the second subset of the array of electronic sensors.

2. The method of claim 1, wherein each of the electronic sensors includes a field effect transistor having a gate electrode; and wherein the sensor electrode is in electrical communication with the first subset of the array of electronic sensors through fluid, and an output of the sensor electrode is in electrical communication with the gate electrodes of the field effect transistors of the second subset of the array of electronic sensors.

3. The method of claim 1, wherein the array of electronic sensors is arranged in rows and columns, and wherein the second subset of the array of electronic sensors includes a column of electronic sensors, and an output of the sensor electrode is in electrical communication with each electronic sensor within the column of electronic sensors of the second subset of the array of electronic sensors.

4. The method of claim 1, further comprising:

applying a reference voltage through a solution in fluid communication with the flow cell in fluid communication with the first subset of the array of electronic sensors.

5. The method of claim 4, wherein the reference voltage is applied by a reference electrode.

6. The method of claim 1, wherein the array of electronic sensors includes field effect transistors.

7. The method of claim 6, wherein the field effect transistors include ion sensitive field effect transistors.

8. The method of claim 1, further comprising:

flowing a solution through the sensor electrode;

measuring a third response of the sensor electrode through the solution; and amplifying the third response of the sensor electrode.

9. The method of claim 8, further comprising:

providing an offset to the third response of the sensor electrode to center the third response relative to a reference voltage.

10. The method of claim 1, wherein the first response of the first subset of the array of electronic sensors is adjusted by scaling and subtracting the second response of the second subset of the array of electronic sensors.

\* \* \* \* \*